(12) United States Patent
Dai et al.

(10) Patent No.: US 8,795,734 B2
(45) Date of Patent: Aug. 5, 2014

(54) HYDROPHOBIC NANOTUBES AND NANOPARTICLES AS TRANSPORTERS FOR THE DELIVERY OF DRUGS INTO CELLS

(75) Inventors: Hongjie Dai, Cupertino, CA (US); Nadine Wong Shi Kam, Ann Arbor, MI (US); Paul A. Wender, Menlo Park, CA (US); Zhuang Liu, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 13/566,740

(22) Filed: Aug. 3, 2012

(65) Prior Publication Data
US 2013/0034610 A1   Feb. 7, 2013

Related U.S. Application Data

(62) Division of application No. 11/431,346, filed on May 9, 2006, now Pat. No. 8,246,995.

(60) Provisional application No. 60/679,374, filed on May 10, 2005.

(51) Int. Cl.
*A61K 9/16*   (2006.01)
*A61K 9/50*   (2006.01)
*A61K 38/54*  (2006.01)
*A61K 39/00*  (2006.01)
*B82Y 5/00*   (2011.01)
*C12N 15/11*  (2006.01)
*A61K 48/00*  (2006.01)

(52) U.S. Cl.
USPC ....... 424/491; 424/94.3; 424/178.1; 977/906; 977/746; 977/773; 977/840; 514/44 R; 514/1.1; 514/44 A

(58) Field of Classification Search
USPC ................................... 977/906, 746
See application file for complete search history.

(56) References Cited

U.S. PATENT DOCUMENTS

| | | | |
|---|---|---|---|
| 5,091,187 A * | 2/1992 | Haynes | ........... 424/450 |
| 6,187,823 B1 | 2/2001 | Haddon et al. | |
| 6,896,864 B2 | 5/2005 | Clarke | |
| 7,009,033 B2 | 3/2006 | Varshney et al. | |
| 7,070,810 B2 | 7/2006 | Hirsch et al. | |

(Continued)

FOREIGN PATENT DOCUMENTS

| | | |
|---|---|---|
| EP | 1605265 A1 | 12/2005 |
| WO | 02095099 A1 | 11/2002 |
| WO | 2004089818 A1 | 10/2004 |

OTHER PUBLICATIONS

Sigma-Aldrich Product Information for BSA (CAS No. 9048-46-8) (May 2, 2000).*

(Continued)

*Primary Examiner* — Cherie M Stanfield
(74) *Attorney, Agent, or Firm* — David J. Aston; Peters Verny, LLP

(57) ABSTRACT

Methods and materials for delivering biologically active molecules to cells in vitro or in vivo are provided. The methods and materials use carbon nanotubes or other hydrophobic particles, tubes and wires, functionalized with a linking group that is covalently bound to the nanotubes, or, alternatively, to the biologically active molecule, such as a protein. The biologically active molecule is preferably released from the nanotube when the complex has been taken up in an endosome.

18 Claims, 10 Drawing Sheets

(56) References Cited

U.S. PATENT DOCUMENTS

| | | | |
|---|---|---|---|
| 7,731,929 | B2 | 6/2010 | Clarke |
| 7,968,073 | B2 | 6/2011 | Clarke et al. |
| 2002/0150524 | A1 | 10/2002 | Smalley et al. |
| 2002/0179434 | A1 | 12/2002 | Dai et al. |
| 2003/0012723 | A1 | 1/2003 | Clarke |
| 2005/0031526 | A1 | 2/2005 | Clarke |
| 2005/0037075 | A1* | 2/2005 | Farokhzad et al. ........... 424/468 |
| 2005/0100960 | A1 | 5/2005 | Dai et al. |
| 2005/0229335 | A1 | 10/2005 | Huang et al. |
| 2006/0018826 | A1 | 1/2006 | Unger et al. |
| 2006/0199770 | A1 | 9/2006 | Bianco et al. |
| 2006/0275371 | A1 | 12/2006 | Dai et al. |
| 2007/0117109 | A1 | 5/2007 | Rothemund |

OTHER PUBLICATIONS

Kam, Nadine Wong Shi, et al., "Carbon Nanotubes as Intracellular Protein Transporters: Generality and Biological Functionality," J. Am. Chem., 2005, vol. 127, 6021-6026.

Won Seok Seo, et al., "FeCo/graphitic-shell nanocrystals as advanced magnetic-resonance-imaging and near-infrared agents," Nature Materials, 2006, vol. 5, 971.

Zhang Liu, et al., "siRNA Delivery into Human T Cells and Primary Cells with Carbon-Nanotube Transporters," Angew. Chem. Int. Ed., 2007, vol. 46, 2023-2027.

Kam, Nadine Wong Shi, "Biological Applications of Carbon Nanotubes: Paving the Way to Nanotube-Based Delivery Vehicles and Therapies for Living Systems," Stanford University Dissertation, May 2006, ProQuest Information and Learning Company.

Chen, et al., Noncovalent Sidewall Functionalization of Single-Walled Carbon Nanotubes for Protein Immobilization, J. Am. Chem. Soc., 2001, vol. 123, 3838-3839.

Int'l. Appl. No. PCT/US08/71032, International Search Report, Oct. 10, 2008, 2 pp.

Elkins, et al., (ChemBioChem, May 1, 2005 epub 6;640-643.

Williams, et al., (Nature, Dec. 19-26, 2002; 420(6917):761).

Bianco et al., (J.AM. Chem. Soc. Dec. 16, 2004 epub. 127;58-59.

Dwyer et al. "DNA-functionalized single-walled carbon nanotubes", Nanotechnology, 2002;13:601-604.

Nadine Wong Shi Kam, et al. "Nanotube Molecular Transporters: Internalization of Carbon Nanotube—Protein Conjugates in Mammalian Cells", J. Am. Chem. Soc., May 13, 2004, 126, 6850-6851.

Nadine Wong Shi Kam, et al., "Carbon Nanotubes as Intracellular Transporters for Proteins and DNA: An Investigation of the Uptake Mechanism and Pathway," Agnew. Chem., 2006, 118, 591-595, published online Dec. 13, 2005.

Nadine Wong Shi Kam, et al., "Carbon Nanotubes as Intracellular Transporters for Proteins: Generality and Biological Functionality," J. Am. Chem. Soc., 2004, 126(22): 6850-6851, published online Mar. 31, 2005.

Nadine Wong Shi Kam, et al., "Carbon nanotubes as multifunctional biological transporters and near-infrared agents for selective cancer cell destruction," PNAS, Aug. 16, 2005, vol. 102, No. 33, 1600-11605.

Nadine Wong Shi Kam, et al., "Functionalization of Carbon Nanotubes via Cleavable Disulfide Bonds for Efficient Intracellular Delivery of siRNA and Potent Gene Selencing," J. Am. Chem. Soc., 2005, 127, 12492-12493.

Jian Chen, et al., "Solution Properties of Single-Walled Carbon Nanotubes," Science, 1998, vol. 282, 95-98.

Weissleder, et al., "In vivo imaging of tumors with protease-activated near-infrared fluorescent probes," Nature Biotechnology, 1999, vol. 17, 375-378.

Wang, et al., "Surface Chemistry and Electrical Properties of Cermanium Nanowires," J. Am. Chem. Soc., 2004, 126, 11602-1611, published online Aug. 25, 2004.

Cherukuri, et al., "Near-Infrared Fluorescence Microscopy of Single-Walled Carbon Nanotubes in Phagocytic Cells," J. Am. Chem. Soc., 2004, vol. 16, 16-17, publised online Nov. 3, 2003.

Pantarotto, et al., "Translocation of bioactive peptides across cell membranes by carbon nanotubes," Chem. Commun., 2004, vol. 16, 16-17, publised online Nov. 3, 2003.

Chen, et al., "Noncovalent functionalization of carbon nanotubes for highly specific electronic biosensors," PNAS, 2003, vol. 100, No. 9, 4984-4989.

Bianco, "Carbon nanotubes for the delivery of therapeutic molecules," Expert Opin. Drug Deily. Nov. 2004, vol. 1, No. 1, 57-65.

Felekis, et al., "Single-Walled carbon nanotube-based hybrid materials for managing charge transfer processes," Rev. Adv. Mater. Sci. Aug. 2005, 10, 272-276.

Zheng, et al., "Structure-based carbon nanotube sorting by sequence-dpendent DNA assembly," Science, 2003, vol. 302, 1545-1548.

Wang, et al., "Peptides with selective affinity for carbon nanotubes," Nature Materials, 2003, online, 196-200.

Menna, et al., "Shortened single-walled nanotubes functionalized with poly(ethylene glycol): preparation and properties," ISSN, 2003, xiii, 64-73.

Chou, et al., "Optical characterization of DNA-wrapped carbon nanotube hybrids," Chemical Physics Letters, Sep. 16, 2004, 397, 296-301.

Gruner, "Carbon nanotube transistors for biosensing applications," University of California Los Angeles and Nanomix Inc., Emeryville CA, at www.physica.ucla.edu/research/biophysics/pubs/paper 2006.

* cited by examiner

Fig. 3A
Fig. 3B
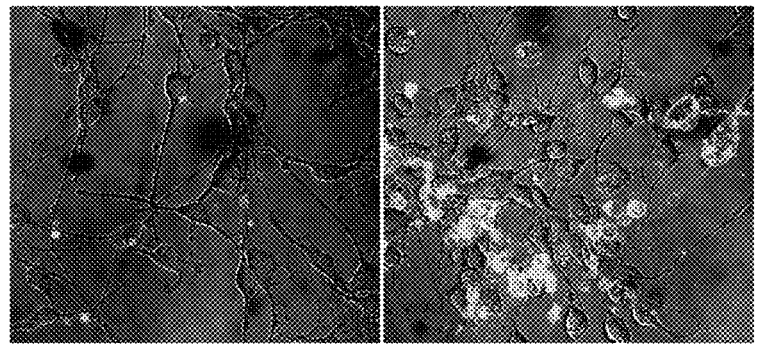
Fig. 3C
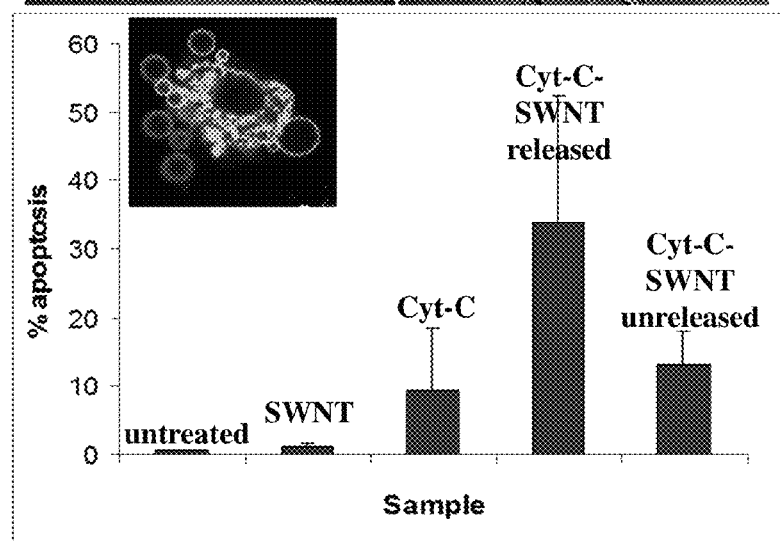

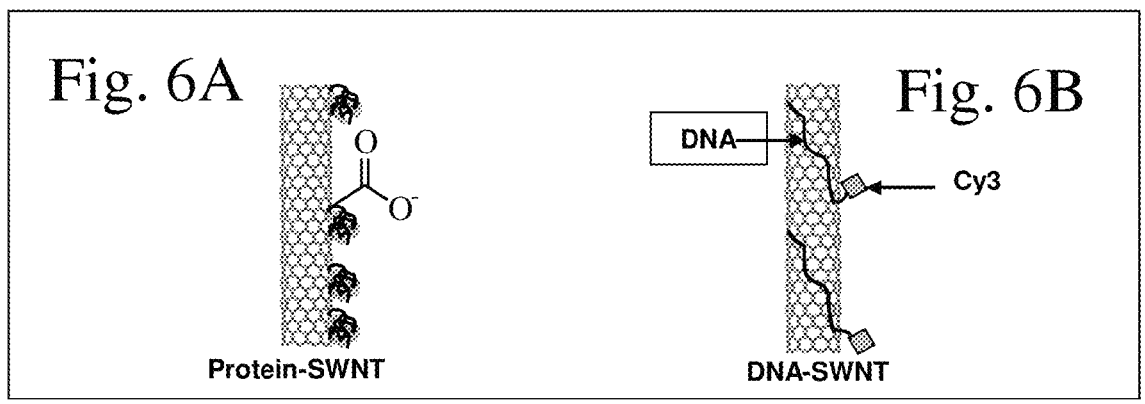
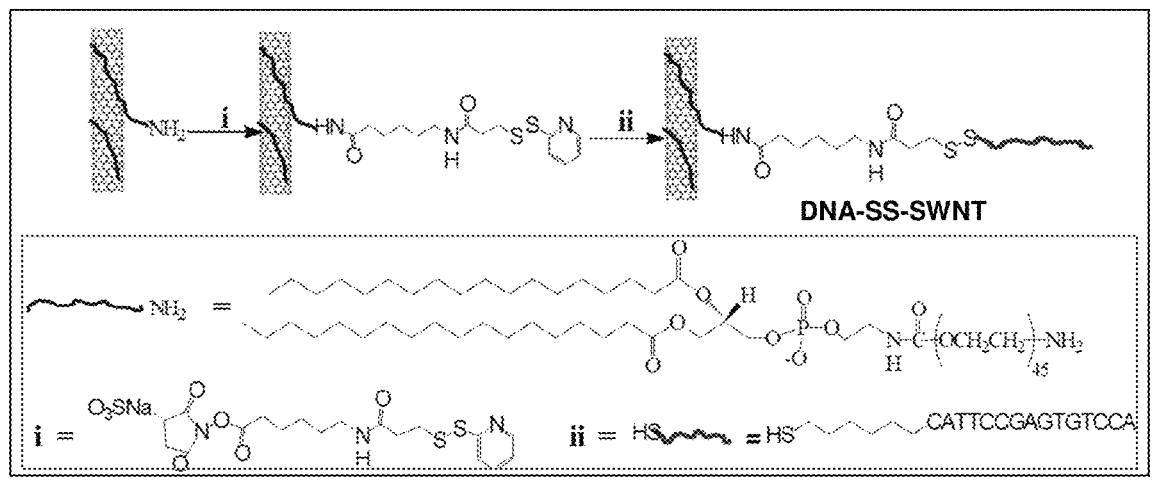
Fig. 6C

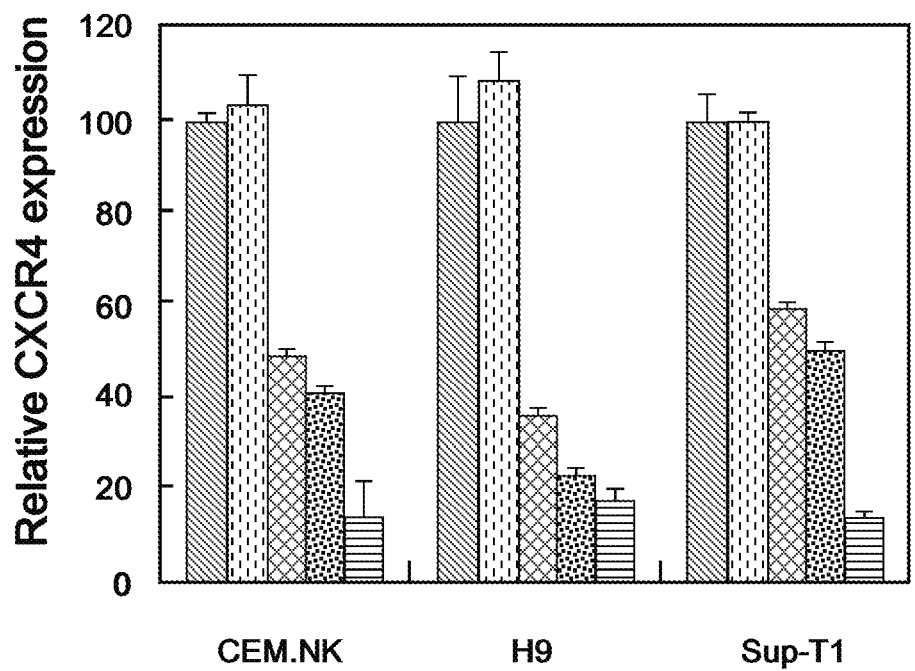
Fig. 8 Relative Expression of CXCR

Fig. 9A-9B Cell viability of 4188 cells

SEQUENCE LISTING

```
<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cattccgagt gtcca                                                         15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cattccgagt gtcca                                                         15

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gaucaagaga cuccucagug a                                                  21

<210> SEQ ID NO 4
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
acugaggagu cucuugauct g                                                   21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
gcggcagcag guagcaaagt t                                                   21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
cuuugcuacc ugcugccgct t                                                   21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
gaacaucauc auccaggact t                                                   21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cuggacuucc agaagaacat t                                                   21

<210> SEQ ID NO 9
<211> LENGTH: 21
<212> TYPE: DNA
<213> ORGANISM: Artificial Sequence
```

-continued

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ttgaccugaa ggucuucuug u                                              21
```

HYDROPHOBIC NANOTUBES AND NANOPARTICLES AS TRANSPORTERS FOR THE DELIVERY OF DRUGS INTO CELLS

CROSS-REFERENCE TO RELATED APPLICATIONS

This application claims priority to U.S. Provisional Patent Application 60/679,374, filed May 10, 2005, and is a divisional of U.S. patent application Ser. No. 11/431,346 filed on May 9, 2006, now U.S. Pat. No. 8,246,995, both of which are hereby incorporated by reference.

STATEMENT OF GOVERNMENTAL SUPPORT

This invention was made with Government support under contracts CA 031841 and CA 031845 awarded by the National Institutes of Health and contract 0213618 awarded by the National Science Foundation. The Government has certain rights in this invention.

REFERENCE TO SEQUENCE LISTING, COMPUTER PROGRAM, OR COMPACT DISK

Applicants submit herewith a sequence listing in an ASCII text file (3815_07_2_seq_list.txt), as provided in EFS Legal Framework Notice 20 May 2010, part I-I-1. The file was created Jul. 23, 2012 and contains 2,163 bytes. Applicants incorporate the contents of the sequence listing by reference in its entirety.

BACKGROUND OF THE INVENTION

1. Field of the Invention

The present invention relates to the field of nanoparticles, particularly carbon nanotubes and other nanoparticles and also to the field of cellular uptake of exogenous drugs or agents such as polypeptides, polynucleotide or small molecules with poor cellular uptake, and also to the fields of primary cell and T cell delivery.

2. Related Art

The interaction between nanostructured materials and living systems is of fundamental and practical interest and will determine the biocompatibility, potential utilities and applications of novel nanomaterials in biological settings. The pursuit of new types of molecular transporters is an active area of research, due to the high impermeability of cell membranes and other biological barriers to foreign substances and the need for intercellular delivery of molecules via cell-penetrating transporter for drug, gene or protein therapeutics (Henry, C. M. Chem. Eng. News 2004, 82, 37; Smith, D. A.; vandeWaterbeemd, H. Curr. Opion. Chem. Biol. 1999, 3, 373; Bendas, G. Biodrugs 2001, 15, 215). Recently, we and others (Kam, N. W. S.; Jessop, T. C.; Wender, P. A.; Dai, H. J. J. Am. Chem. Soc. 2004, 126, 6850; Pantarotto, D.; Briand, J.; Prato, M.; Bianco, A. Chem. Comm. 2004, 1, 16; Lu, Q.; Moore, J. M.; Huang, G.; Mount, A. S.; Rao, A. M.; Larcom, L. L.; Ke, P. C. Nano Lett. 2004, 4, 2473; Cherukuri, P.; Bachilo, S. M.; Litovsky, S. H.; Weisman, R. B. J. Am. Chem. Soc. 2004, 126, 15638; Bianco, A.; Hoebeke, J.; Godefroy, S.; Chaloin, O.; Pantarotto, D.; Briand, J.-P.; Muller, S.; Prato, M.; Partidos, C. D.; 16 Dec. 2004, W. R. D. J. Am. Chem. Soc. 2005, 127, 58) have uncovered the ability of single-walled carbon nanotubes (SWNTs) to penetrate mammalian cells and further transport various cargos inside cells including small peptides (Pantarotto), the protein streptavidin (Kam) and nucleic acids (Lu, Bianco). In our work of nanotube internalization and streptavidin transporting using nanotube carriers (Kam) and the work of Cherukiri et al., on nanotube uptake, the internalization mechanism was attributed to endocytosis. In the work of Pantarotto et al., Bianco et al., and Lu et al., nanotube uptake was suggested to be via insertion and diffusion through the lipid bilayer of cell membrane. While the uptake mechanism is unclear, it has been consistently reported that well-processed water-soluble nanotubes exhibit no apparent acute cytotoxicity to all living cell lines investigated thus far.

Covalent and non-covalent sidewall functionalization of single-walled carbon nanotubes (SWNT) has been actively pursued in recent years (Acc. Chem. Res. 2002, 35, Special issue on carbon nanotubes), aimed at several important goals. The first is to impart solubility to nanotubes in various solvents needed for dispersion, manipulation, sorting and separation. The second is to impart chemical functionality to nanotubes by attaching organic, inorganic or biological species to facilitate the interfacing of nanotubes with other materials for useful composites or bioconjugates. Functionalization of SWNTs with highly hydrophilic groups has been sought after in order to render nanotubes soluble in aqueous solutions. This would allow interfacing nanotubes with biological systems, potentially leading to an understanding of the biocompatibility (Mattson, M. P.; Haddon, R. C.; Rao, A. M. J. Mol. Neurosci. 2000, 14, 175-182) of nanotubes and the development of interesting biological applications including biosensors (Chen, R.; Zhang, Y.; Wang, D.; Dai, H. J. Am. Chem. Soc. 2001, 123, 3838-3839; Chen, R. J.; Bangsaruntip, S.; Drouvalakis, K. A.; Kam, N. W. S.; Shim, M.; Li, Y. M.; Kim, W.; Utz, P. J.; Dai, H. J., "Noncovalent functionalization of carbon nanotubes for highly specific biosensors," Proc. Nat. Acad. Sci. USA. 2003, 100, 4984-4989). Various methods have been reported on modifying the sidewalls of the SWNTs to achieve solubility in water, including covalent functionalization by acid treatment (Chen, J.; Hammon, M. A.; Hu, H.; Chen, Y. S.; Rao, A. M.; Eklund, P. C.; Haddon, R. C. Science 1998, 282, 95-98), and physical adsorption of polymers, surfactants and nucleic acids (Chen, R. J.; Bangsaruntip, S.; Drouvalakis, K. A.; Kam, N. W. S.; Shim, M.; Li, Y. M.; Kim, W.; Utz, P. J.; Dai, H. J. Proc. Nat. Acad. Sci. USA. 2003, 100, 4984-4989; O'Connell, M. J.; Boul, P.; Ericson, L. M.; Huffman, C.; Wang, Y.; Haroz, E.; Kuper, C.; Tour, J.; Ausman, K.; Smalley, R. E. Chem. Phys. Lett. 2001, 342, 265-271; Moore, V. C.; Strano, M. S.; Haroz, E. H.; Hauge, R. H.; Smalley, R. E. Nano Lett. 2003, 3, 1379-1382).

It has now been surprisingly found that non-covalent functionalization of SWNTs can be accomplished by binding proteins to the nanotubes by various mechanisms, including strong adsorption of phospholipids grafted with polyethylene glycol (PEG) chains, which renders the nanotubes highly water-soluble. Previously, PEG-phospholipids (PEG-PL) have been investigated in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464). In a recent work, Norris and coworkers have shown that PEG-PLs are excellent surfactants for solubilizing CdSe nanocrystals in aqueous phases Dubertret, B.; Skourides, P.; Norris, D. J.; Noireaux, V.; Brivanlou, A. H.; Libchaber, A. Science 2002, 298, 1759-1762).

Bianco EP 1 605 265, (published Dec. 14 2005), "Non-covalent complexes comprising carbon nanotubes," relates to the use of a carbon nanotube comprising positive and/or negative charges, said charges being carried by at least one charge-carrying group, said charge-carrying group being covalently bound to the surface of said carbon nanotube. Bianco further describes several non-covalent complexes between carbon nanotubes and various molecules, such as DNA or proteins, which have been described in the prior art. In most instances, the molecules and the carbon nanotubes are bound together through hydrophobic and/or π-stacking interactions.

Zheng, et al., (2003) Nature Mater. 2: 338-342 describe the solubilization of carbon nanotubes by single stranded DNA molecules, wherein the DNA molecule wraps helically around the carbon nanotube through π-stacking interactions to form a soluble complex. See also, Zheng, et al., "Structure-Based Carbon Nanotube Sorting by Sequence-Dependent DNA Assembly," Science 29:1545-1548 (November 2003).

Dai, et al., WO 02/095099 (published Nov. 28, 2002 and related to PNAS 100:4984 cited above, as well as US PGPUB 2005/0100960) relates to complexes formed from the irreversible adsorption of molecules to the sidewalls of carbon nanotubes through π-stacking, van der Waals and hydrophobic interactions. As shown in FIG. 1 of the US PGPUB 2005/0100960, plurality of noncovalently-bonded molecules, having a highly aromatic group such as a pyrenyl group, are configured and arranged for bonding to additional molecules, such as biomolecules such as antibodies, antigens and DNA. These complexes are intended for in vitro use, e.g., as biosensors, where the attached molecules do not dissociate from the nanotubes.

Chen et al., PNAS 100:4989 (2003) shows the binding of various proteins (Steptavidin, avidin, BSA, staphylococcal protein A and α-glucosidase) to as-grown nanotubes, and nanotubes treated with surfactants such as Tween, Pluronic P103 and Triton-X. It was reported that a monolayer of Tween 20 anchored on a nanotube would repel non-specific binding of proteins in solution. Ten different polypropylene oxide molecules were investigated for their ability to adsorb onto nanotube walls.

One drawback associated with such complexes is that the dissociation of the complex is either difficult and/or has not been soundly assessed.

Another drawback associated to those complexes is that once dissociated from the complex, the carbon nanotube by itself is not soluble in aqueous systems and tends to form hydrophobic aggregates, which precipitate. Besides, non-functionalized carbon nanotubes have been shown to be toxic in several instances (Warheit et al., (2004) Toxicological Sciences 77:117-125; Lam et al., (2004) Toxicological Sciences 77: 126-134; Shvedova et al., (2003) Journal of Toxicology and Environmental Health, Part A 66:1909-1926).

Bianco et al., "Functionalized Carbon Nanotubes, A Process For Preparing the Same and Use in Medicinal Chemistry," WO 2004/089818 (published 21 Oct. 2004) discloses functionalized carbon nanotubes of the general formula $[C_n]—X_m$ where Cn are surface carbons of a carbon nanotube, X is a functional group and n and m are integers such that there are from about $2.10^{-11}$ to about $2.10^{-9}$ moles of X per cm$^2$ of nanotube surface. The surface atoms $C_n$ are reacted to form, as X, a pyrrolidine ring, bound to the nanotube by two different C—C bonds.

Hannah, US PGPUB 2004/0110128, published Jun. 10, 2004, entitled "Carbon Nanotube Molecular Labels," discloses that carbon nanotubes may be derivatized with reactive groups to facilitate attachment to analytes or probes. Nanotubes may be derivatized to contain carboxylic acid groups (U.S. Pat. No. 6,187,823). Carboxylate derivatized nanotubes may be attached to nucleic acid probes or other analytes by standard chemistries, for example by carbodiimide mediated formation of an amide linkage with a primary or secondary amine group located on a probe or analyte. The methods of derivatization and cross-linking are not limiting and any reactive group or cross-linking methods known in the art may be used.

US PGPUB 20040038251 to Smalley, et al., published Feb. 26, 2004, entitled "Single-wall carbon nanotubes of precisely defined type and use thereof," discloses coating nanotubes with a possibly toxic surfactant to prevent interaction with other nanotubes, and that the surfactant may be BRIJ® surfactants (BRIJ is a registered trademark of ICI Americas, Inc.; examples of BRIJ surfactants are polyethylene glycol dodecyl ether, polyethylene glycol lauryl ether, polyethylene glycol hexadecyl ether, polyethylene glycol stearyl ether, and polyethylene glycol oleyl ether), PLURONIC®. Surfactants (PLURONIC is a registered trademark of BASF Corporation); and other surfactants.

Dwyer, et al., "DNA functionalized single-walled carbon nanotubes," Nanotechnology 13:601-604 (2002) discloses linking DNA to nanotubes through amino-terminated DNA strands. A lambda DNA cluster is shown attached to a defect site and ends of an SWNT bundle.

Felekis, et al., "Single-walled carbon nanotube-based hybrid materials for managing charge transfer processes," Rev. Adv. Mater. Sci. 10:272-276 (205) discloses formation of nanohybrids consisting of SWNT units and electron donor moieties such as porpyrinic and ferrocenyl units.

Menna et al., in a conference paper dated Oct. 1, 2003, "Shortened single-walled nanotubes functionalized with poly (ethylene glycol): preparation and properties," disclose the grafting of PEG onto SWNTs after acid oxidative cutting, treatment with SOCl2 to yield SWNT-COCL, and amidation with PEG-monoamine.

BRIEF SUMMARY OF THE INVENTION

The present invention entails methods and materials directed to the uptake by living cells, preferably mammalian cells, of active agents which typically have poor cellular uptake, such as polypeptides and polynucleotides and certain small molecules with poor cellular uptake or bioavailability.

The present method involves the delivery of an effective amount of an active agent to a living cell. A stable suspension is prepared comprising suspended carbon nanotubes. The nanotubes are then complexed with the active agent by means of certain bifunctional linkers. The complex is applied to a cell in vitro or administered in vivo as an aqueous suspension whereby the cell takes up an effective amount of the complex, including the active agent. The present methods and materials are well suited to delivery of agents to cells that are difficult to transfect by other means. These include primary cells and cultured cell lines, especially including cell types such as leukocytes such as T cells, and cancer cells.

One aspect of the present invention involves the preparation of carbon nanotubes that are stable in an aqueous environment. The nanotubes must not be agglomerated, i.e., they must exist as single tubes or groups of <10 tubes. They are sized and disaggregated by a series of steps including the step of sonicating the carbon nanotubes. The sizes must be controlled and are about 50 and 500 nm long and 1-5 nm in diameter. They may be between 50 and 1500 nm long and 1-5 nm in diameter. The diameter depends on the degree of agglomeration (bundling) and the exact dimension of the nanotube used. Although the term "nanotube" is used throughout the present description of the preferred embodiment, other nanoparticles may be adapted for the present transport complexes, given the present teachings, and any use of the term "nanotube" in the description should not be construed as limiting the invention to nanotubes.

The present nanotube complexes include those wherein the active agent is a polynucleic acids or a polypeptide. The polypeptide may be any biologically active structure and may be selected from the group consisting of enzymes, antibodies, peptides, and transcription factors. These materials are well known, and may be obtained commercially, e.g., from EMD Biosciences, Inc, an Affiliate of Merck KGaA, Darmstadt, Germany. The present methods and material are applicable to polypeptides having a very low molecular weight, (e.g., 1 kD) up to those with a molecular weight between 20 kD and 150 kD and higher. One active agent may be a protein, which induces apoptosis. Uptake of cytochrome c and subsequent apoptosis is demonstrated. The polynucleic acid may be among a wide variety of biologically active polynucleotides, and may be selected from the group consisting of mRNA, dsRNA, RNAi, synthetic DNA encoding a polypeptide, synthetic DNA complementary to a regulatory region of the cell, and cDNA encoding a polypeptide.

One aspect of the present method involves the use of pH change to release a bound agent from the complex. The agent is complexed to an acid labile linkage and the pH is lowered to release the agent after it has been taken up by the cell. The relatively more acidic environment of the endosome, where the present complexes are shown to be directed, facilitates acidic release. The pH may also be raised by agents such as chloroquine, which is a quinine malaria drug known to raise cellular pH. Other pH modulators are known to raise cellular pH, such as $NH_4Cl$ and BafA1. One may also administer pH-lowering agents, such as lactic acid, to cleave acid labile linkages.

Specific cleavable linkages contemplated by the present invention include disulfide and hydrazone linkages.

The carbon nanotubes used in the invention are preferably SWNTs but MWNTs or doped or modified nanotubes or even nanospheres may be used. The active agent is coupled to the carbon nanotube through a bifunctional linker. The bifunctional linker serves to carry the agent into the cell with the nanotube, but releases the agent after the complex is taken up. The bifunctional linker therefore is either covalently or non-covalently linked to either the nanotube or the active agent. The bifunctional linker may be selected from the group consisting of a nanotube carbonyl group (covalent linkage), a lipid aliphatic group, a lipid aliphatic group coupled to PEG and an affinity molecule, wherein the affinity molecule is selected from the group consisting of: biotin, nickel, iron, calcium, zinc, GSH, ATP, GTP, GDP, ADP, NADH, boronic acid and an oligonucleotide. Embodiments employing biotin should have the biotin covalently linked to the nanotube, which again, may be done through a carbonyl group on the nanotube. By providing an acidic (carbonyl) group on a nanotube carbon, linking agents can be attached to the carbonyl carbon or the carbonyl group can itself serve as a link to polypeptide or other active agents. Other affinity molecules are known to bind non-covalently to various proteins, such as ATP to kinases, etc.

In one aspect, the present invention comprises the preparation of a complex comprising a hydrophobic nanoparticle and a linker molecule having a hydrophobic portion adsorbed onto the particle (e.g., a phospholipid), a hydrophilic portion for solubility (e.g., PEG) and a cargo linked to the hydrophilic portion. These methods and materials exploit a delivery mechanism as determined by the present inventors that involves hydrophobic interactions between nanoparticles and cell surfaces, as opposed to electrostatic interactions used by conventional agents, such as liposomes. Thus the delivery method is applicable to any hydrophobic interaction mediated cell surface association, and subsequent endocytosis and cargo delivery.

BRIEF DESCRIPTION OF THE DRAWINGS

FIG. 3(A) is a photograph showing a confocal image of NIH-3T3 cells with cytochrome c alone (no SNWT); 3(B) is a photograph showing a confocal image of NIH-3T3 cells with cytochrome c, SNWTs in the presence of chloroquine; and 3(C) is a graph showing apotosis response under various conditions;

FIG. 6A, 6B, 6C is a schematic of (6A) protein-SWNT and (6B) DNA-SWNT conjugates. Lower panels (6C) show functionalization scheme of SWNT with PEG-PL-$NH_2$ and subsequent formation of disulfide linkage to form DNA-SS-SWNT conjugate. A photograph of an aqueous solution of DNA-SS-SWNT is also shown;

FIG. 8 is a graph of relative CXCR4 expression level of control cells (first bar, lipo-siRNA treated cells after 3 days incubation (second bar, NT-SS-siRNA treated cells after 1 day (third bar), 2 days (fourth bar) or 3 days (fifth bar) incubation;

DETAILED DESCRIPTION OF THE PREFERRED EMBODIMENT

Definitions

Figure 1:
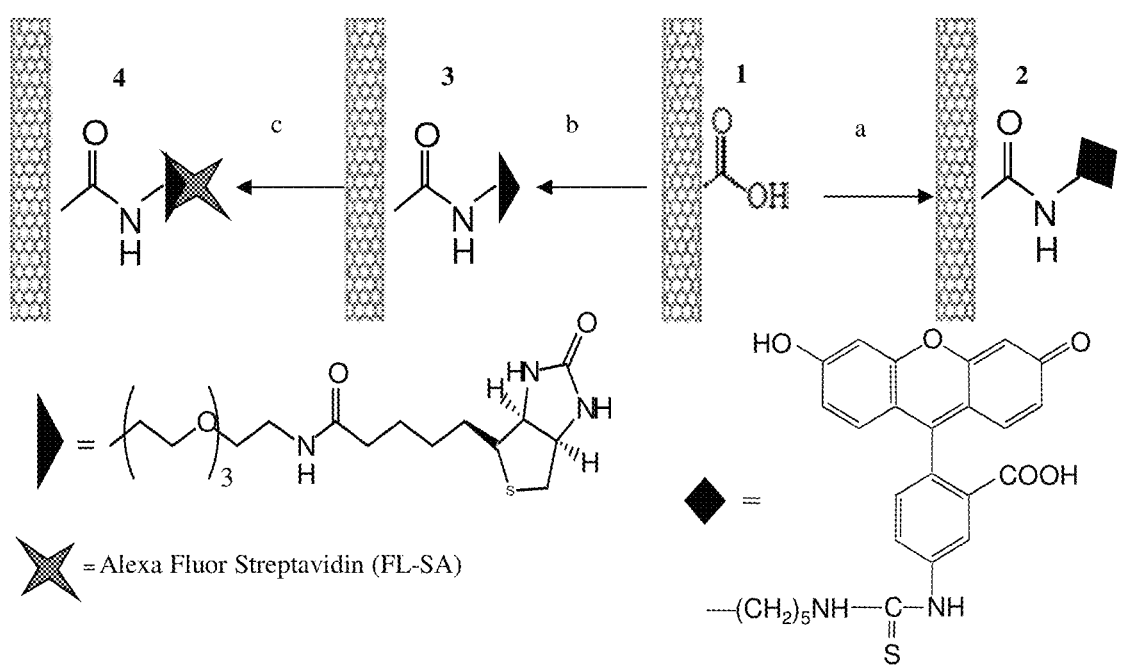
FIG. 1 is a schematic view of acid functionalization and protein coupling through biotin-strepavidin binding. A nanotube is shown in four stages of functionalization beginning with structure 1 and continuing to structures 2-4.

The following definitions are intended to clarify the meanings of certain terms used herein. In general, unless specifically contradicted below, all scientific terms are used in their customary and accepted technical sense.

The term "active agent" means a polypeptide, polynucleotide or poorly absorbed small molecule that imparts some activity to a cell which takes up the agent. The activity may be a marker activity, as in the uptake of a fluorescent probe, or it may be a metabolic activity such as apoptosis. Preferably the active agent is biologically active. The agent may modulate any number of biological functions in the cell, such as cell division, a cellular infection, cellular expression of cell surface proteins, cellular response to a hormone such as insulin, etc. The term "biologically active" further refers to polynucleotides, small molecules, and polypeptides which cause a metabolic change in a cell, generally by increasing transcription, expression or translocation of one or more genes, or by binding to an expressed protein.

The term "carbon nanotube" means a tube that contains a sheet of graphene rolled into a cylinder as small as 1 nm in diameter. Both single-walled nanotubes (SWNTs) and multiwalled nanotubes (MWNTs), with many concentric shells, have been synthesized. The electronic properties of a nanotube depend on the angle (chirality) with which it is rolled up—the present nanotubes can be metals, small-gap semiconductors, or large-gap semiconductors. Carbon nanotubes may include other materials. Metallic tubes have shown ballistic conduction on length scales of a micron or more. Nanotubes are also the stiffest known material, with a Young's modulus of ~1 TPa, which makes them excellent candidates for nanomechanical systems. Carbon nanotubes, as used herein, include structures that are not entirely carbon, such as BCN nanotubes. The present carbon nanotubes may also be graphene in other forms. This includes a single sheet of graphene formed into a sphere, which constitutes a carbon nanosphere, commonly referred to as a buckyball or fullerene.

The term "cleavable linkage" means a chemical bond that is cleaved under physiological conditions in a cell. Examples of cleavable linkages include disulfide bonds, diester bonds, azo groups (cleavable with dithionate), sulfones (cleavable with basic phosphate, with or without dithiothreitol), glycols, cleavable by periodate, hydrozone, and the like.

A further discussion of cleavable linkages which may be adapted for use in the present invention, according to the present teachings, is found in Kosak "Biocleavable micelle compositions for use as drug carriers," U.S. Pat. No. 6,835,718, hereby incorporated by reference. As stated there, a suitable biocompatible linkage comprises the disulfide linkages that are well known for covalently coupling drugs to polymers. However, they may be cleaved in the bloodstream rather than in the cell. The simple ester bond is another type that includes those between any acid and alcohol. Another type is any imidoester formed from alkyl imidates. Also included are maleimide bonds as with sulfhydryls or amines used to incorporate a biocleavable linkage. Another category comprises linkages or bonds that are more specifically cleaved after entering the cell (intracellular cleavage). The preferred linkages for release of drugs within the cell are cleavable in acidic conditions like those found in lysosomes. One type is an acid-sensitive (or acid-labile) hydrazone linkage as described by Greenfield, et al, Cancer Res. 50, 6600-6607 (1990), and references therein. As is known and as used herein, a hydrazone linkage is of the formula R—C=N—NH—X, where R or X is the cargo and the other group is the hydrophilic linker. Another type of preferred acid-labile linkage is any type of polyortho or diortho ester linkage, examples disclosed by J. Heller, et al., Methods in Enzymology 112, 422-436 (1985), J. Heller, J. Adv. Polymer Sci. 107, 41 (1993), M. Ahmad, et al., J. Amer. Chem. Soc. 101, 2669 (1979) and references therein.

The term "nanoparticle" means a material having the properties of a carbon nanotube insofar as the material is a hydrophobic material having a diameter on the order of the diameter of an MWNT (preferably 10-20 nm, not more than 100 nm) or smaller, and length not more than about 20 µm, preferably of not more than 50-500 nm in length, are atomically ordered and are generally chemically inert, such as a nanowire (see, e.g., "Controlled growth of highly uniform, axial/radial direction-defined, individually addressable InP nanowire arrays," Premila Mohan et al 2005 Nanotechnology 16 2903-2907, and US PGPUB 20050221083 to Belcher, et al., published Oct. 6, 2005, entitled "Inorganic nanowires," hereby incorporated by reference, fullerenes, fullerenols, etc. The term "nanoparticle is also intended to include nanostructured materials <100-1000 nm in at least one of the three dimensions such as\tubes, wires, particles and crystals. The term nanoparticle also includes carbon black, whose primary particles range in size from 10 nm to 500 nm. Carbon blacks are commercially available in a variety of particle sizes and morphologies. The term "nanoparticle" also includes hydrophobic polymeric particles, such as spheres of nanoparticle size. i.e. less than 1000 nm, e.g., polystyrene beads of 20, 50 or 100 nm as exemplified below. The term "hydrophobic polymer" is used herein to mean any polymer resistant to wetting, or not readily wet, by water, i.e., having a lack of affinity for water. A hydrophobic polymer typically will have a surface free energy of about 40 dynes/cm ($10^{-5}$ Newtons/cm or N/cm) or less. Examples of hydrophobic polymers include, by way of illustration only, polylactide, polylactic acid, polyolefins, such as polyethylene, poly(isobutene), poly(isoprene), poly(4-methyl-1-pentene), polypropylene, ethylenepropylene copolymers, and ethylenepropylene-hexadiene copolymers; ethylene-vinyl acetate copolymers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers. Further examples are given in U.S. Pat. No. 6,673,447, hereby incorporated by reference.

The term "polypeptide" means a peptide or protein. A "peptide" can include a peptide-based therapeutic drug. Peptides are comprised of a range of amino acids consisting from several up to about 70 amino acids, and have a molecular mass up to 10 kDa. Clinically useful peptides include Th1-activating thymosin, gp41-binding HIV-fusion inhibitory peptide T-20, intestinal structure/function-enhancing GLP-2, pancreatic islet neogenesis associated INGAP peptide, parathyroid hormone and food intake inhibitory peptide PYY3-36 among others. These examples are presently marketed or in various stages of clinical development.

The term "protein" means a natural or artificial polypeptide that has a biological activity in its native state, i.e., it can be denatured and lose activity. This includes biologically active peptides and proteins consisting of natural amino acids and their synthetic analogues L, D, or DL configuration at the alpha carbon atom selected from valine, leucine, alanine, glycine, tyrosine, tryptophan, tryptophan isoleucine, proline, histidine, lysin, glutamic acid, methionine, serine, cysteine, glutamine phenylalanine, methionine sulfoxide, threonine, arginine, aspartic acid, asparagine, phenylglycine, norleucine, norvaline, alpha-aminobutyric acid, O-methylserine, O-ethylserine, S-methylcysteine, S-benzylcysteine, S-ethylcysteine, 5,5,5-trifluoroleucine and hexafluoroleucine. Also included are other modifications of amino acids, which include but are not limited to, adding substituents at carbon atoms such as —OH, —SH, —SCH₃, —OCH₃, —F, —Cl, —Br, OR—NH₂. The peptides can be also glycosylated and phosphorylated. The natural biologically active proteins include but are not limited to: enzymes (such as DNA polymerases, RNA polymerases, esterases, lipases, proteases, kinases, and transferases), transcription factors, transmembrane proteins, membrane proteins, cyclins, cytoplasmic proteins, nuclear proteins, toxins and hormones. These proteins have an MW greater than 700 Daltons. Their MW is preferably between 12 and 80 kD, and may be extended to include large proteins, including full size IgG molecules of about 150 kD. In the preferred methods of the invention, an amino or carboxy end of the polypeptide is coupled to a linking agent (e.g., PEG, biotin, or acid oxide).

The term "polynucleotide" means a polymeric form of nucleotides of at least about 10 bases or base pairs in length, either ribonucleotides or deoxynucleotides or a modified form of either type of nucleotide, and is meant to include single and double stranded forms of DNA and/or RNA. As is known in the art, such polynucleotides typically have two termini, a 3' and a 5' end. In the preferred methods of the invention, a first end of the polynucleotide is coupled to a linking agent (e.g., PEG, biotin, or acid oxide). The polynucleotide may be coupled to a detectable marker such as a fluorophore. The polynucleotide is biologically active in that it imparts an additional property to a cell that has taken up the polynucleotide, such as fluorescence, or the known properties associated with RNAi, antisense DNA, or gene therapy or DNA vaccines.

Briefly, RNAi is thought to involve the following components: dsRNA corresponding to a portion of a gene to be silenced is introduced into a cell. The dsRNA is digested into 21-23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA.about.12 nucleotides from the 3' terminus of the siRNA (reviewed in Sharp et al (2001) Genes Dev 15: 485-490; and Hammond, et al., (2001) Nature Rev Gen 2: 110-119). RNAi (RNA interference) through the administration of double stranded RNA is further defined and explained in U.S. Pat. No. 6,506,559 to Fire, et al., Jan. 14, 2003, hereby incorporated by reference. SiRNA molecules may be designed to any expressed gene according to known principles. For example, Ambion supplies a free online tool, "siRNA Target Finder." In general, Ambion scientists find that ~50% of siRNAs designed using this tool will reduce target gene expression by >50%.

Ribozymes are further included in the present polynucleotides and are further defined and explained in U.S. Pat. No. 5,616,459 to Kramer, et al., issued Apr. 1, 1997, hereby incorporated by reference.

Suitable polynucleotides also include antisense molecules, as manufactured, e.g., by Isis Pharmaceuticals or described in Bartelmez, et al. U.S. Pat. No. 6,869,795, "Antisense compositions and cancer-treatment methods," hereby incorporated by reference. Antisense oligonucleotides typically have modified ribose rings or backbone linkages to facilitate binding to the target mRNA.

The term "polar lipid" refers to a molecule having an aliphatic carbon chain with a terminal polar group. Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Further polar lipids are exemplified in U.S. Pat. No. 6,339,060, "Conjugate of biologically active compound and polar lipid conjugated to a microparticle for biological targeting," to Yatvin, et al., hereby incorporated by reference.

The term "phospholipid" means a molecule having an aliphatic carbon chain with a terminal phosphate group. Typically the phospholipids will comprise a glycerol backbone, attached to two fatty acid (aliphatic groups) esters and an alkyl phosphate. Suitable phospholipids for use in this invention include, without limitation, dimyristoyl phosphatidylcholine, distearoyl phosphatidylcholine, dilinoleoyl-phosphatidylcholine (DLL-PC), dipalmitoyl-phosphatidylcholine (DPPC), soy phophatidylchloine (Soy-PC or PCs) and egg phosphatidycholine (Egg-PC or PCE). Suitable phospholipids also include, without limitation, dipalmitoyl phosphatidylcholine, phosphatidyl choline, or a mixture thereof. Exemplified below are 1,2-dipalmitoyl-sn-glycero-3 phosphoethanolamine phospholipid and 1,2-Distearoyl-sn-Glycero-3-Phosphoethanolamine.

The term "aliphatic," as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl" and the like. Furthermore, as used herein, the terms "alkyl," "alkenyl," "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The aliphatic (lipid) alkyl groups employed in the lipids of the invention preferably contain 4-20, more preferably 10-20 aliphatic carbon atoms. In certain other embodiments, the lower alkyl, (including alkenyl, and alkynyl) groups employed in the invention contain 1-10 aliphatic carbon atoms. Illustrative aliphatic groups thus include, but are not limited to, for example, methyl, ethyl, n-propyl, isopropyl, cyclopropyl, —CH₂-Cyclopropyl, allyl, n-butyl, sec-butyl, isobutyl, tert-butyl, cyclobutyl, —CH₂-cyclobutyl, n-pentyl, sec-pentyl, isopentyl, tert-pentyl, cyclopentyl, —CH₂-cyclopentyl-n, hexyl, sec-hexyl, cyclohexyl, —CH₂-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like. The aliphatic groups are hydrophobic and adsorb to the hydrophobic nanoparticle.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —N(R')$_2$, wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

The term "drug" means an "active agent" that is a biologically relevant molecule including DNA, RNA, proteins, peptide, polypeptide or polynucleotide or a small molecule that normally has poor cellular uptake by themselves. Cellular uptake is measured by intracellular concentration in target cells or organs, e.g., by immunofluorescence, confocal microscopy or flow cytometry or radio imaging. Suitable small molecule drugs include cyclosporine, buprenorphine, oxybutynin, or other molecules with poor bioavailability.

The term "PEG" means Polyethylene glycol, a polymer with the structure (—CH$_2$CH$_2$O—)$_n$ that is synthesized normally by ring opening polymerization of ethylene oxide. The PEG used herein will impart water (and serum) solubility to the hydrophobic nanoparticle and lipid portion of the polar lipid. The polymer is usually linear at molecular weights (MWs) ≤10 kD. The PEG used here will have an MW below 5,400, preferably below 2,000, or about 45 repeating ethylene oxide units. However, the higher MW PEGs (higher "n" repeating units) may have some degree of branching. Polyethylene glycols of different MWs have already been used in pharmaceutical products for different reasons (e.g., increase in solubility of drugs). Therefore, from the regulatory standpoint, they are very attractive for further development as drug or protein carriers. The PEG used here should be attached to the nanoparticles at a density adjusted for the PEG length. For example, with PL-PEG 2000, we have an estimate of ~4 nm spacing between PEG chain along the tube. At this spacing, PEG5400 is too long and starts to block interaction with cell surface. For PEG at ~1 nm distance, the PEG MW should be less than about 200, to allow hydrophobicity.

For coupling proteins to PEG, usually monomethoxy PEG [CH$_3$ (—O—CH$_2$—CH$_2$)$_n$—OH] is first activated by means of cyanuric chloride, 1,1'-carbonyldiimidazole, phenylchloroformate, or succidinimidyl active ester before the addition of the protein. In most cases, the activating agent acts as a linker between PEG and the protein, and several PEG molecules may be attached to one molecule of protein. The pharmacokinetics and pharmacodynamics of the present nanotubes-PEG-protein conjugates are expected to be somewhat dependent on the MW of the PEG used for conjugation. Generally the presently used PEG will have a molecular weight of approximately 100-2,000 Daltons.

The present PEG may also modified PEG such as PolyPEG® (Warwick Effect Polymers, Ltd., Coventry, England) is new range of materials suitable for the attachment of polyethylene glycol (PEG) to therapeutic proteins or small molecules. These are prepared using Warwick Effect Polymers' polymerization technology, (See U.S. Pat. No. 6,310, 149) and contain terminal groups suitable for conjugation with, among other things, lysine, terminal amino and cysteine residues.

The term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of caspase-mediated disorders, as described generally above.

The term "stable" means a solution or suspension in a fluid phase wherein solid components (i.e., nanotubes and drugs) possess stability against aggregation sufficient to allow manufacture and delivery to a cell and which maintain the integrity of the compound for a sufficient period of time to be detected and preferably for a sufficient period of time to be useful for the purposes detailed herein.

The term "effective amount" means a sufficient amount of agent to cause a detectable decrease in the condition to be modulated in the cell, or in increase in the desired effect, e.g., detectability of acellular process. It may reduce the severity of the disease or in caspase activity and/or cell apoptosis, as measured by any of the assays described in the examples herein. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage.

The expression "dosage unit form" means a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics," Tenth Edition, A. Gilman, J. Hardman and L. Limbird, eds., McGraw-Hill Press, 155-173, 2001, which is incorporated herein by reference in its entirety).

The term "primary cell" is used in its conventional sense, i.e. a cell that is derived directly from an organism or tissue, with a limited number of passages in culture.

The term "leukocyte" is used in its conventional sense and The term leukocyte refers to a mixture of white blood cell types obtained from peripheral blood, lymph or organs such as the thymus, spleen or lymph nodes and peritoneal exudate. The term mononuclear cell refers to those leukocytes separated by a density gradient technique, usually employing, for example, LSM® solution (lymphocyte separating medium, a mixture of sodium metriazoate and epichlorohydrin-sucrose polymer), and consisting of lymphocytes and monocytes (also known as macrophages when found in tissue). Monocytes (macrophages) are large, adherent highly phagocytically active mononuclear cells. Lymphocytes are relatively small nondescript cells responsible for antibody production and capable of becoming cytotoxic cells with proper stimulation. The other major type of leukocytes are the granulocytes, also characterized as polymorphonuclear cells (PMN'S); Neutrophil refers to the most common type of granulocyte in peripheral blood and is characterized by its ability to phagocytize foreign bodies. All of these cells are identified primarily by histologic staining techniques and their behavior during density gradient sedimentation.

The term "T cell" is used in its conventional sense and refers to a type of lymphocyte. The term "T cell" is intended to include thymocytes, immature T lymphocytes, mature T lymphocytes, resting T lymphocytes, or activated T lymphocytes. The T cells can be $CD4^+$ T cells, $CD8^+$ T cells, $CD4^+$ $CD8^+$ T cells, or $CD4^-$ $CD8^-$ T cells. The T cells can also be T helper cells, such as T helper 1 (Th1) or T helper 2 (Th2) cells.

Generalized Methods and Materials

SWNTs and other nanoparticles are shown in the description below to be generic transporters for the intracellular uptake various types of DNA, RNA, siRNA, proteins, polynucleotides, small molecules and polypeptides. As exemplified below, proteins (≤80 kD) were non-covalently and non-specifically bound (NSB) to nanotube sidewalls. The proteins investigated include streptavidin (SA), protein A (SpA), bovine serum albumin (BSA), and cytochrome c (cyt-c). As also exemplified below, siRNA targeting CXCR4 in T cells, myc in lymphoma cells, and other polynucleotides were effectively delivered into cells using the present complexes.

The present carbon nanotubes may be made by a variety of processes including those made by arc discharge, laser ablation, chemical vapor deposition (CVD) and Hipco. Hipco is the High-pressure CO disproportionation process for catalytic production of SWNTs in a continuous-flow gas phase using CO as the carbon feedstock and $Fe(CO)_5$ as the iron-containing catalyst precursor. SWNTs are produced by flowing CO, mixed with a small amount of $Fe(CO)_5$ through a heated reactor. Size and diameter distribution of the nanotubes can be roughly selected by controlling the pressure of CO.

Multiple walled nanotubes can be made by chemical vapor deposition or arc discharge. Size-controlled, soluble SWNT's are described, for example in Czerw, et al., "Organization of Polymers onto Carbon Nanotubes: A route to Nanoscale Assembly, NanoLetters 1(8):4230427 (2001).

Other known manufacturing processes can be used. Carbon nanotubes are generally produced by three main techniques, arc discharge, laser ablation and chemical vapor deposition. In arc discharge, a vapor is created by an arc discharge between two carbon electrodes with or without catalyst. Nanotubes self-assemble from the resulting carbon vapor. In the laser ablation technique, a high-power laser beam impinges on a volume of carbon-containing feedstock gas (methane or carbon monoxide). At the moment, laser ablation produces a small amount of clean nanotubes, whereas arc discharge methods generally produce large quantities of impure material. In general, chemical vapor deposition (CVD) results in MWNTs or poor quality SWNTs. The SWNTs produced with CVD have a large diameter range, which can be poorly controlled. But on the other hand, this method is very easy to scale up.

Another aspect of the present nanotubes is that they are controlled in size and aggregation (i.e., bundling). The sizes are between 50 and 500 nm in length, and clumps are between a single tube (~1 nm) to clumps of 5 nm. This is done by rinsing and sonication, as described in detail below. The specific steps described may be routinely varied in time, temperature, concentration, etc. in accordance with the present teachings. The nanotube rinsing and sonication provides a stable nanotube suspension. In a preferred process, the nanotubes are optionally refluxed in very low pH (<2) oxidizing acid, sonicated to cut the nanotubes into short segments, refluxed in strong acid again and filtered, rinsed and resuspended and reacted in suspension with the linking agent. Oxidation, if used, is adjusted to produce about 0.5 to 2 oxidized sites per nm length of nanotube.

The intracellular protein transporting and uptake via nanotube carriers are also shown here to be generic for various adherent and non-adherent mammalian cell lines including HeLa, NIH-3T3 fibroblast, HL60 and Jurkat cells. The delivery is also generic for human and animal T cell lines and primary cell lines. The latter are well known to be difficult to deliver molecules into by conventional drug delivery agents such as liposomes. Energy dependent endocytosis is demonstrated as an internalization mechanism. This provides a means for controlling endocytosis and subsequent release of the present complexes. Further, with cytochrome c as the cargo protein, we present an exploration of the fate of internalized protein-SWNT-protein conjugates, attempts of releasing the conjugates from the endosome vesicles into the cell cytoplasm using chloroquine, and investigation of the biological functions of the released proteins. We observe apoptosis or programmed cell death induced by cyt-c transported inside cells by SWNTs after release from the endosomes. The results provide the first proof of concept of in vitro biological functionality and activity of proteins delivered by SWNT molecular transporters. Agents which modify apoptosis are known in the art, and include proteins such as p53, p21WAF1, Myc, Bcl-2, Bax, and Bak, as well as small molecules such as actinomycin D, 5-fluorouracil, etc., as well as antisense and siRNA approaches, e.g., silencing X-linked inhibitor of apoptosis (XIAP), which is the most potent member of the IAP gene family in terms of its ability to inhibit caspases and suppress apoptosis. (See, Clinical Cancer Research Vol. 9, 2826-2836, July 2003). In general, the complexes described here utilize a carboxyl or carbamide functionality on the nanotubes or a lipid (aliphatic) functionality that is hydrostatically bound to the nanotubes. These serve as bifunctional linkers between nanotubes and polynucleotides, polypeptides or small molecules that would otherwise not penetrate a cell membrane.

The present biological proteins may be coupled though a biotin-avidin system, as described in detail below. In this case, the protein is avidin. However, other protein-binding pairs may be exploited wherein a protein has a high binding affinity for a relatively small molecule. For example, ATP, as discussed below, may also be coupled to the nanotubes, and used to non-covalently couple enzymes, which utilize ATP as a co-factor. GTP, GDP, ADP, NADH or other nucleotides or nucleotide analogs may also be so employed. Oligonucleotides may be used to conjugate DNA or RNA binding proteins.

Various enzyme inhibitors can be used to non-covalently bind their cognate enzymes. Small molecule neurotransmitters or neurotransmitter mimetics may be used to deliver proteins that bind to these neurotransmitters.

The biologically active protein will be conjugated to the smaller molecule, which is linked to the nanotubes through one of the chemistries described below. Other small molecules that may be used are metals such as iron, calcium, or zinc. Again, there are biologically active proteins (hemoglobin, calmodulin, "zinc-finger" transcription factors, etc.) that bind to metals.

Antibodies may be linked to nanotubes by acid labile groups linked to the cognate antigen of the antibody. The term "antibody" is intended to cover antibody variations, such as single chain antibodies, FAb fragments, and the like.

These material are linked to a protein to be delivered, or, in some cases, may be used to deliver small molecules that are otherwise impermeable to cells. Because the uptake of the present complexes is by endocytosis, receptor-mediated uptake can be employed. This means that receptor ligands can be used as nanotubes payloads or coupling agents. As an example of an alternative embodiment, Arkin, et al., "Binding of small molecules to an adaptive protein-protein interface," PNAS, Feb. 18, 2003, Vol. 100(4) 1603-1608, describes a small molecule that binds to IL-2. Such a small molecule could be covalently linked to the present lipid and released in a cell, or could be used to bind IL-2 for delivery into a cell by being linked to a bifunctional linker compound on the nanotubes, i.e., the carboxy or carbamide group.

Other bifunctional linkers may be used instead of the exemplified biotin-strepavidin complex. For example, nickel complexes may be coupled to nanotubes and complexed to his-tagged proteins. Bound nucleotides may be used to complex protein kinases, GTPases. Etc. Reduced glutathione (GSH) may be covalently coupled to nanotubes and complexed to proteins containing a glutathione S-transferase (GST) fusion tag. Boronic acid may be used for ribonucleoside binding. Heparin may be used to bind heparin-binding proteins (e.g., ATIII).

The foregoing bifunctional linkers are defined herein as "affinity molecules."

It will be appreciated that the above referenced carboxy or carbamide functions, as well as the exemplified proteins, biotin or other bifunctional linkers, and phospholipids, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of caspase-mediated disorders, as described generally above. In general, the present invention involves the non-covalent conjugation of biological molecules to carbon nanotubes in a preparation, which is taken up by cells and the biological molecule (e.g., protein) remains biologically active.

With regard to releasing a coupled protein inside a cell, Example 15 demonstrates release of the apoptosis-inducing protein cytochrome c by the addition of the malaria drug chloroquine, which is a base. Other schemes could be used which take advantage of the acidic environment of the endosome. For example, the drug to be delivered could be linked via acid-labile phosphoramidite (P—N) bonds. Complexes may also be designed for release by esterases, proteases, phosphatases, reducing agents and the like.

The examples below, particularly examples 24-27, show that nanotube material, when complexed to active agents, is more efficient than conventional transfection reagents in breaching the cellular membrane. Upon entry, SWNT conjugates are able to delivery a siRNA cargo to the cytoplasm of the cells to induce RNAi, thus indicating that the biological activity of the cargo is largely intact. The combination of the transport and delivery capabilities of the SWNT transporter combined with the potency of siRNA-mediated silencing caused knockdown of the myc oncogene in T-cell lymphomas to trigger cell death and adversely affect cell proliferation. The potential of SWNT for gene therapy applications is also demonstrated.

Examples 1-8

Internalization of Carbon Nanotube-Protein Conjugates Comprising Oxidized SWNT-Biotin-Strepavidin Complexes Examples 1-8 below describe experiments conducted in accordance with FIG. 1.

FIG. 1 shows the synthesis and schematic of various SWNT conjugates. The complexes are labeled, left to right, 4, 3, 1, 2. The complex starts as 1. Then, in step a, it is reacted with EDC, 5-(5-aminopentyl) thioureidyl fluorescein, phosphate buffer to yield 2. In step b, 1 is reacted with EDC, biotin-LC-PEO-amine, phosphate buffer to yield 3; in step c, 3 is reacted with fluoresceinated streptavidin to yield 4. Examples 1-10 present our findings on the uptake of single walled nanotubes (SWNT) and SWNT-streptavidin (a protein with clinical applications in anticancer therapies (Hussey, S. L.; Peterson, B. R. *J. Am. Chem. Soc.* 2002, 124, 6265-6273)) conjugates into human promyelocytic leukemia (HL60) cells and human T cells (Jurkat) via the endocytosis pathway. The results described below with HL60 cells appear to be general with other cells as well, including Jurkat, Chinese hamster ovary (CHO) and 3T3 fibroblast cell lines. It has been shown that hydrophobic forces are responsible for nonspecific binding between nanotubes and proteins (Chen, R. J.; Bangsaruntip, S.; Drouvalakis, K. A.; Kam, N. W. S.; Shim, M.; Li, Y. M.; Kim, W.; Utz, P. J.; Dai, H. J. *Proc. Nat. Acad. Sci. USA.* 2003, 100, 4984-4989). Although the nanotubes used in the current work contain negatively charged carboxylates along the sidewalls, such groups are likely only present on defect sites along the tubes. The unoxidized areas of the nanotubes may still afford regions of appreciable hydrophobicity. We propose that the nanotubes non-specifically associate with hydrophobic regions of the cell surface and internalize by endocytosis (Silverstein, S. C.; Steinman, R. M.; Cohn, Z. A. *Annu. Rev. Biochem.* 1977, 46, 669-722; Vida, T. A.; Emr, S. D. *J. Cell Bio.* 1995, 128, 779-792). We detected no green fluorescence from the interior of cells after incubation in 4 at 4° C., consistent with the blockage of endocytosis at 4° C. (Silverstein and Vida). Further, we used a red FM 4-64 marker to stain (Vida; Richard, J. P.; Melikov, K.; Vives, E.; Ramos, C.; Verbeure, B.; Gait, M. J.; Chenomordik, L. V.; Lebleu, B. *J. Biol. Chem.* 2003, 278, 585-590) endosomes formed around nanotubes during endocytosis and observed yellow color inside cells due to overlapping of green fluorescence (SWNT conjugates) and red-stained endosomes. This provides a direct evidence for endocytosis of nanotubes conjugates. The nanotubes appear to accumulate in the cytoplasm in the cells after internalization.

In conclusion, we have prepared modified nanotubes and have shown that these can be derivatized to enable attachment of small molecules and proteins. The functionalized SWNT enter non-adherent as well as adherent cell lines (CHO and 3T3) and by themselves are not toxic. While the fluoresceinated protein SA by itself cannot enter cells, it readily enters cells when complexed to a SWNT-biotin transporter, exhibiting dose dependent cytotoxicity. The uptake pathway is consistent with endocytosis. SWNT could be exploited as molecular transporters for various cargos. The biocompatibility, unique physical, electrical, optical and mechanical properties of SWNT provide the basis for new classes of materials for drug, protein, and gene delivery applications.

As described below, the present complexes utilize nanotubes to carry proteins into cells. Towards this end, 1 was treated with EDC and biotin-LC-PEO-amine followed by dialysis to afford biotin functionalized SWNTs 3; which was then incubated with fluoresceinated streptavidin (SA) to afford SWNT-biotin-SA conjugate 4 (FIG. 1). To evaluate the ability of nanotubes to enable the cellular uptake of the attached protein, HL60 cells were incubated with 4 as described above. Visualization of the SA revealed intense fluorescence inside the cells (data not shown). Importantly, the internalization of SWNT-biotin-SA conjugate 4 illustrates that nanotubes can carry large cargos, in this case SA (MW ~60 KD), and transport them into cells. The uptake of SA was further confirmed by flow cytometry (FC). The fluorescence of cells incubated with SA alone was only slightly greater than the background fluorescence of untreated cells (data not shown). We systematically varied the time of cell incubation of 4 ([SWNT] ~0.05 mg/mL in the solution) and found uptake increased with longer incubations, up to ~4 h. Upon increasing the concentration of 4 in the incubation solution, we observed a monotonic increase in the cellular fluorescence.

To examine the potential toxicity of SWNT, HL60 cells were incubated with 1, 2, 3 and 4 (1 h, 0.05 mg/mL tubes), isolated by centrifugation and observed after 24 and 48 h. In the case of 1, 2, and 3, no appreciable cell death was observed. These results indicate that the functionalized SWNT themselves exhibit little toxicity to HL60 cells.

The SWNT-biotin-SA conjugate 4 however, was found to cause extensive cell death when examined 48 h after the 1 h-incubation with HL60. The degree of cell death was substantial as evidenced by the large amounts of cell debris observed. We found that the onset of appreciable cell death occurred typically ~12 h after the incubation with 4. To further confirm that the toxicity was due to the delivery of SA into cells, the amount of SA on the SWNT was reduced by decreasing the [SA] used to load the SWNT from 2.5 to 0.0625 µM. The observed toxicity was nearly non-existent at [SA]<1.25 µM. The dependence of cell viability on the amount of SA uptake was similar to a previous observation (Hussey). Consistent with the inability of SA to transverse the cell membrane alone, no toxicity was observed after cells were incubated even in highly concentrated solutions of SA. Significantly, these studies show that the SWNTs not only internalize the protein but the internalized conjugate elicits a functional dose dependent response.

Example 1

Preparation, Oxidation and Cutting of SWNT

Stable aqueous suspensions of purified, shortened and functionalized nanotubes were obtained by oxidation and sonication (Chen, J.; Hammon, M. A.; Hu, H.; Chen, Y. S.; Rao, A. M.; Eklund, P. C.; Haddon, R. C. *Science* 1998, 282, 95-98; Liu, J.; Rinzler, A. G.; Dai, H.; Hafner, J. H.; Bradley, R. K.; Boul, P. J.; Lu, A.; Iverson, T.; Shelimov, K.; Huffman, C. B.; Rodriguez-Macias, F.; Shon, Y.-S.; Lee, T. R.; Colbert, D. T.; Smalley, R. E. *Science* 1998, 280, 1253-1256). of laser ablated SWNT. Specifically, SWNTs were refluxed in 2.5 M $HNO_3$ for two 36 h periods separated by cup-horn sonication for 30 min. The resulting mixture was then filtered through a 100 nm pore size polycarbonate filter, rinsed and re-suspended in pure water with sonication. Centrifugation (7000 rpm, 5 min) removed larger unreacted impurities from the solution to afford a stable suspension of 1.

Analysis of 1 by atomic force microscopy revealed mostly short (~100 nm-1 µm) SWNTs with diameters in the range of 1-5 nm corresponding to mostly isolated individual SWNTs and small bundles. No significant amounts of particles were observed on the substrate, suggesting good purity of the SWNTs in solution. Zeta potential measurement revealed a surface potential of ~−75 mV at pH 7 on 1, confirming the existence of numerous negatively charged acidic groups at the sidewalls of the nanotubes. In pure water, 1 was stable for extended periods of time and did not agglomerate. In physiological buffer solutions containing ~0.2 M salt, the suspension was less stable and started to aggregate after 2-3 h.

Besides providing a highly stable aqueous suspension of purified, shortened nanotubes, the oxidation/sonication procedure introduced surface carboxylates on the nanotubes for chemical derivatization. Reaction of 1 with EDC and 5-(5-aminopentyl)thioureidyl fluorescein afforded fluorescein functionalized SWNTs, 2 (FIG. 1).

We used a modified oxidation and cutting procedure based on Chen et al., Science 282:95 (1998) and Liu et al., Science 280:1253 (1998) to treat nanotubes. SWNT (20 mg) grown by laser ablation were mixed with 100 mL of 2.5 M $HNO_3$. The mixture was refluxed for about 36 h, sonicated with a cup-horn sonicator (Branson Sonifer 450) for 30 min, and then refluxed again for another 36 h. After this treatment, the mixture was filtered through a polycarbonate filter (Whatman, pore size 100 nm), rinsed thoroughly and then re-suspended in pure water by sonication. The aqueous suspension was then centrifuged at 7000 rpm for about 5 min to remove any large un-reacted impurities from the solution.

Example 2

Nanotube Characterization

Nanotubes undergone the acid treatment above were characterized by atomic force microscopy (AFM) and zeta potential measurements. For AFM, a silica substrate was first treated with (3-aminopropyl)-triethoxysilane (APTES, Aldrich) to render the surface positively charged. A drop of the nanotube suspension was placed on the substrate and kept for 15 min before blow-dry. The substrate was then imaged by an AFM operated in the tapping mode (Digital Instruments). Zeta potential was measured with a ZetaPALS instrument (Brookhaven Instruments Corporation).

The acid treatment process used here was modified from previous methods (Chen and Liu) and had three main effects to the starting raw SWNT material, namely, purification, cutting of nanotubes and functionalization of nanotube sidewalls with oxygen groups. The latter affords water solubility and reactivity towards further conjugation of other molecules to the nanotubes. Reflux in nitric acid breaks down amorphous carbon, dissolves some of the metal species in the material and introduces acidic groups at defect sites along the sidewalls of the nanotubes. The sonication step is known to cut nanotubes into short lengths. The filtration step after the acid treatments removes the acid from the solution and filter out some of the un-reacted graphitic particles existed in the raw laser-oven nanotube material. We characterized the nanotubes that had undergone this treatment by atomic force microscopy (AFM) and zeta-potential measurements. AFM imaging of the materials deposited on a silicon-oxide substrate from a nanotube solution revealed mostly short (~100 nm-1 µm) SWNT with diameters in the range of 1-5 nm corresponding to mostly isolated individual SWNT and small bundles (FIG. 1a). No significant amount of particles was observed on the substrate, suggesting good purity of short SWNT in the nanotube solution. Zeta potential measurement revealed that the cut SWNT exhibited a surface potential of ~−75 mV at pH 7, confirming the existence of highly negatively charged acidic groups at the sidewalls of the nanotubes.

The shear plane (slipping plane) is an imaginary surface separating the thin layer of liquid bound to the solid surface and showing elastic behavior from the rest of liquid showing normal viscous behavior. The electric potential at the shear plane is called zeta potential. In the first, rough approximation, the electrophoretic mobility (the ratio of the velocity of particles to the field strength), induced pressure difference in electroosmosis, streaming potential and sedimentation potential are proportional to the zeta potential. The stability of hydrophobic colloids depends on the zeta potential: when the absolute value of zeta potential is above 50 mV the dispersions are very stable due to mutual electrostatic repulsion and when the zeta potential is close to zero the coagulation (formation of larger assemblies of particles) is very fast and this causes a fast sedimentation. Thus, the present nanotubes complexes will have a zeta potential above about 50.

In pure water, the oxidized cut SWNT were stable for extended periods of time without agglomeration. The nanotubes were less stable in buffer solutions, and typically aggregated within 2-3 h when exposed to physiological buffer solutions containing ~0.2 M salt.

Example 3

Conjugation of Molecules and Proteins to Oxidized SWNT through Biotin

Fluorescently labeled SWNT were obtained by reacting the oxidized and cut SWNT with EDC (1-Ethyl-3-(3-dimethylaminopropyl)carbodiimide hydrochloride) and 5-(5-aminopentyl)thioureidyl) fluorescein, dihydrobromide salt (Molecular Probes) to afford SWNT-fluorescein (compound 2, FIG. 1a). A suspension of the oxidized and cut SWNT in 0.1M phosphate buffer (pH=7.4) at a concentration of 0.2 mg/mL were also mixed and reacted overnight with 1-ethyl-3-(3-dimethylamino-propyl) carbodiimide, EDC (10-20 mM) (Fluka chemicals) and biotin-LC-PEO amine (1 mM) (Pierce chemicals) to afford biotinylated SWNT (3, FIG. 1b). The resulting solution was then dialyzed against H2O in a 14-16K MWCO membrane (Spectrapor) for 3 days to remove excess EDC and biotin-LC-PEO amine reagents. The solution was then reacted with 2.5 µM of Alexa Fluor 488 labeled streptavidin (Molecular Probes) for 1 h to afford SWNT-biotin-SA conjugates (4, FIG. 1c, fluorescence due to the Alexa Fluor labeled SA). All of our functionalized SWNT (2 to 4) were kept in stock solutions in pure water at a concentration of 0.1 mg/ml Note that the conjugation of SA to SWNTs in the current work is through biotin. The protein attachment is therefore non-covalent although the SA-biotin binding is quite strong. An alternative approach is to link proteins to SWNTs via cleavable disulfide bonds.

Example 4

Treatment of Living Cells with Nanotube Solutions (Oxidized/Biotin/Streptavidin)

To visualize the interaction of nanotubes with cells, fluorescently labeled nanotubes 2 (0.05 mg/mL) in SWNT were incubated with HL60 cells for 1 h at 37° C. The cells were washed twice, collected by centrifugation, and resuspended in growth medium. Confocal microscopy revealed appreciable fluorescence on the surface and, more importantly, in the cell interior.

HL60 and Jurkat cells were both grown in RPMI-1640 cell culture medium (Invitrogen) supplemented with 10% fetal bovine serum (FBS). Prior to incubation, the cells were collected by centrifugation and resuspended in RPMI medium at a cell density of 3µ 106 cells/mL. Incubation of cells in a nanotube solution was done by mixing 100 µL of the cell suspension with 100 µL of a SWNT solution (2, 3 or 4) at 37° C. unless otherwise stated. The concentration of SWNT in the incubation solution was ~0.05 mg/mL unless otherwise stated, and the incubation duration was always 1 h in 5% CO2 atmosphere except for time dependent incubation experiments. After incubation, the cells were washed and collected by centrifugation twice, and resuspended in RPMI medium.

Example 5

Measuring the Loading of Proteins on SWNTs

The number of proteins attached to nanotubes can be estimated as follows. The defect density on an as-grown SWNT is about 1 per 500 nm in length. However, it has been shown that sonication in acids creates significant amount of defects, and a defect density or carboxylic acid group density of 1 per 10 nm is reasonable (mean distance between defects is about 10 nm). The specific surface area of a SWNT is A ~1600 m2/g. These suggest that the maximum loading of protein on the oxidized tubes is ~$2.5 \times 10^{19}$ proteins per gram of SWNTs, $N=A/(\pi d \times 1 d)$, where d=2 nm is the tube diameter. The maximum number of proteins loaded onto 1 g of SWNT can therefore be ~40 µmole/g. Our typical protein conjugation experiment involves proteins at concentrations [SA]<2.5 µM and nanotube concentration of [SWNT]=0.1 mg/mL, which corresponds to 25 µmole/g (protein/SWNT) and is below the maximum loading capacity of 40 µmole/g. Therefore, varying the concentration of protein in the experimental range (0.0625 µM to 2.5 µM) will be effective in changing the loading of proteins on SWNTs, since the nanotubes are in excess relative to the proteins.

Example 6

Membrane and Endosome Staining of Cells Exposed to Nanotube Solutions

FM4-64 (Molecular Probes Inc.) is a classical marker used for staining membrane and endosomes. The cell incubations were carried out under similar conditions as discussed in the previous section, except that FM 4-64 (2% v/v) was added to the incubation mixture. The hour-long incubation of HL-60 cells with carbon nanotubes conjugate was carried out on ice (approximate temperature 4° C.). The isolation and rinsing of the cells were achieved as described above.

In order to elucidate the mechanism of entry of the CNT conjugate into the cells, the incubations were carried out in the presence of the membrane and endosome marker FM 4-64 and at low temperatures. FM 4-64 has been previously shown to be an effective marker for endocytosis (Vida, Richard) by specifically staining (red) the endosomes involved in the endocytosis uptake. After the incubation of the cells with both conjugate 4 (FIG. 1) and FM 4-64, we observed red fluorescence (due to FM 4-64 stained endosomes) around green fluorescence (due to nanotube conjugates) in the cell interior. The regions stained red and green overlap each other well (data not shown), thereby indicating that the fluorescence observed from the green CNT-conjugate is located inside the endosomes (red). These results provide direct evidence for the endocytosis uptake pathway.

In order to further confirm endocytosis as the internalization mechanism, we carried out two different incubations of the cells with CNT-conjugate 4 concurrently at 37° C. and 4° C., both in the presence of the FM 4-64. The level of fluorescence observed in the low temperature incubation is drastically lower than the 37° C. incubation. Furthermore, the absence of both the red FM 4-64 dye and the green CNT-conjugate from the cell interior indicate that the uptake of both the dye (well established to undergo endocytosis at 37° C. but blocked at 4° C. (Vida, Richard)) and the nanotube conjugate are blocked at 4° C., thereby confirming that the nanotubes conjugate do get internalized via endocytosis when at 37° C.

Example 7

Confocal Microscopy and Flow Cytometry Imaging of Cells Incubated in Nanotube Solutions Show that the Conjugates have Low Toxicity and do not Compromise Cell Viability Except when Streptavidin is Included All confocal images were taken immediately after the incubation and washing steps, except for the cell viability assay described below. 20 µl of the cell suspension was dropped onto a glass cover slide and imaged by a Zeiss LSM 510 confocal microscope.

Also, cells were analyzed by a Becton-Dickinson FACS-can instrument after incubation in various nanotube solutions. The cell suspension was supplemented with 2% propidium iodide (PI, Fluka chemicals) prior to the measurement. PI is a membrane impermeable dye and does not stain live cells. It can enter dead cells and intercalate into DNA, thereby selectively staining the dead cells red. We carried out dual detection of red and green fluorescence with the cells. The data presented here represent the mean green fluorescence obtained with a population of 10,000 live cells.

By cell cytometry: We used the PI staining method to identify dead cells, if any, caused by exposure of the cells to various nanotube solutions. After incubation of cells in a nanotube solution for 1 h, the cells were washed and re-suspended in RPMI medium. The cells were returned to the 37° C. incubator and observed at different time intervals by confocal microscopy method. For confocal microscopy, the cells were observed at 24 h interval for a period of 48 h. The cells were stained by PI immediately prior to analysis. For the cell cytometry, the cells were observed immediately after the initial incubation with either conjugate 3 or 4 (FIG. 1) and the level of cell death was compared with control cells by PI staining Cell viability was also probed by microscopy. 48 h after the 1 h incubations of HL60 cells in 3 (SWNT-biotin) and 2 (SWNT-fluorescein) respectively, we did not observe any appreciable cell death. Cells were also observed to survive after incubation in solutions of the as-oxidized and cut tubes (without further conjugation to other molecules). These results suggested that the nanotubes themselves (and the ones conjugated with biotin or fluorescein ligands) exhibited little toxicity effects to the HL60 cells. The SWNT-biotin-SA (streptavidin) conjugate (4 in FIG. 1) however, was found to cause extensive cell death when examined 48 h after the hour-long incubation of HL60 in 4. The degree of cell death was drastic as evidenced by the observation of large amount of disintegrated cell debris (FIG. 3b). Since the nanotubes themselves were not toxic as discussed above, and incubation of cells in a solution of SA molecule alone did not lead to any cell death, the observed toxicity after incubation in 4 should be due to the streptavidin cargos transported inside cells via the nanotube carriers. We found that the onset of appreciable cell death occurred typically ~12 h after the incubation in 4 for 1 h and then washing step. We also varied the SA concentration from 2.5 to 0.0625 µM during the SA conjugation step to reduce the amount of proteins attached to the nanotubes, and found that the toxicity effect and cell death were nearly non-existent for [SA]<1.25 µM. Such cell viability dependence on the amount of SA uptake was similar to a previous observation, reported in Hussey, S. L.; Peterson, B. R. *J. Am. Chem. Soc.* 2002, 124, 6265-6273.

The drastically reduced cell viability after incubation in 4 did further signal the internalization of the nanotubes-biotin-streptavidin conjugates with the nanotubes acting as efficient transporters. Streptavidin alone was unable to traverse the cell membrane and therefore no toxicity effects were observed after cells were incubated even in highly concentrated pure SA solutions.

We also monitored cell viability by flow cytometry. The HL60 cells were monitored by flow cytometry after incubation in conjugate 4 (SWNT-biotin-SA). A higher level of PI staining was observed in cells immediately after the hour-long incubation with conjugate 4 (data not shown), whereas the cells that were incubated with conjugate 3 (SWNT-biotin, no SA) showed a minimum level of cell death similar to the untreated cells. These results further confirm that the nanotubes themselves (and SWNT-biotin conjugates) do not affect cell viability, and that the extensive cell death observed after exposure to conjugate 4 is due to the large amount of internalized streptavidin. We also carried out an additional incubation of the HL60 cells with conjugate 4, for longer period of times. After a five-hour long incubation, dramatically higher level of PI staining was observed from the cells.

Example 8

Effects of Nanotube Concentration to the Internalization of Streptavidin and Cell Viability We carried out a set of incubations with conjugate 4 (containing streptavidin, SA, FIG. 1) for which the [SA] was kept constant at 2.5 µM, while the [SWNT] was varied from 0.01-0.2 mg/ml. Viability of the cells was examined immediately following the incubation. The level of the PI staining detected appeared insensitive to the concentration of nanotubes for [SWNT]>0.05 mg/ml. This is consistent with the observation that the amount of nanotubes in this concentration range is in excess relative to proteins, and the amount of proteins carried inside cells are on the same order for the different nanotube concentrations. Cell death is reduced for low [SWNT]=0.01 and 0.025 mg/ml, since the loading of proteins onto the dilute tube solution is reduced from the [SWNT]>0.05 mg/ml cases. These results also indicate that increases in nanotubes concentration do not cause more cell death in the range studied.

Examples 9-16

Figure 2:
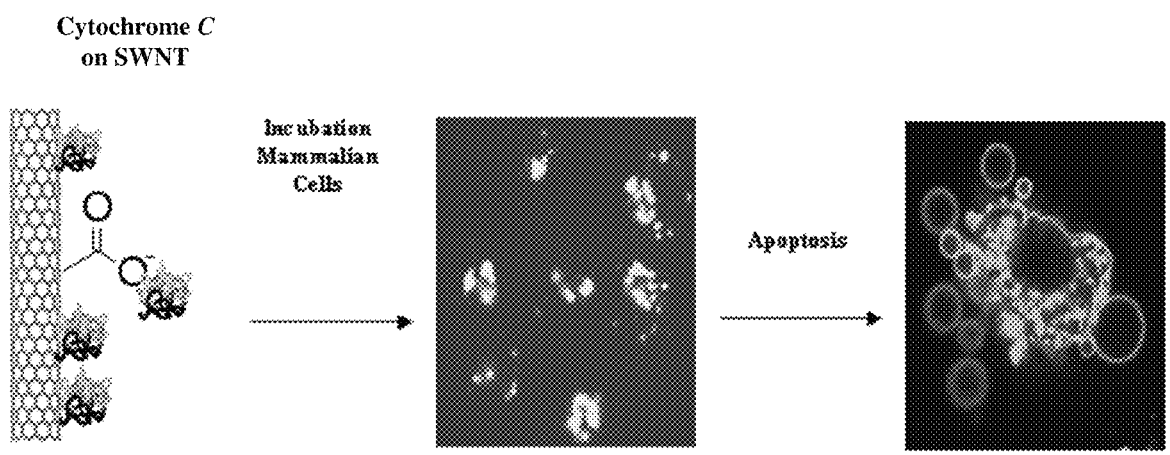
FIG. 2 is schematic diagram with two photographs of incubation of cytochrome c on an SWNT bearing carbonyl groups, and subsequent cellular uptake and apoptosis.

Conjugation Directly to Oxidized Nanotubes and Hydrophobic Interaction; Biological Activity and Release from Endosomes of an Apoptotic Protein In Examples 9-16, the protein to be delivered is linked through a functional group on the nanotubes. As shown in FIG. 2, acidic oxygen groups on the side of SWNT's rendered them soluble. These groups also provide anchors for electrostatic interactions with surface residues on proteins, namely positively charged amino acids, e.g., lysine or arginine. Hydrophobic regions of proteins also bind directly to the carbon surface.

Example 9

Purification, Cutting and Oxidation of SWNTs

Similar to the steps described previously, SWNTs (20 mg) grown by laser ablation were mixed with 100 mL of 2.5 M $HNO_3$, refluxed for about 36 h, sonicated with a cup-horn sonicator (Branson Sonifer 450) for 30 min to cut the nanotubes into short segments and refluxed again for another 36 h. After this treatment, the mixture was filtered through a polycarbonate filter (Whatman, pore size 100 nm), rinsed thoroughly and then re-suspended in pure water by sonication. The aqueous suspension was then centrifuged at 7000 rpm (revolutions per minute) for about 5 min to remove any large impurities from the solution. SWNTs after these processing steps were in the form of short (tens to hundreds nanometers) individual tubes (~1.5 nm in diameter) or small bundles (up to 5 nm in diameter) and re-suspended to give a concentration of ~0.04-0.05 mg/mL. Acidic oxygen groups (e.g., —COOH) on the sidewalls of the tubes rendered solubility or high suspension stability of the SWNTs in water and buffer solutions.

Example 10

Conjugation of Proteins Directly to Oxidized SWNTs

Alexa-fluor 488-labeled streptavidin (SA, molecular weight 60 kD), alexa-fluor bovine serum albumin (BSA, 66 kD) were purchased from Molecular Probes Inc. Protein A (42 kD), cytochrome c (12 kD) and Fluorescein isothiocyanate-labeled human immunoglobin G (hIgG, 150 kD) were obtained from Aldrich. Cyt-c and SpA were fluorescently labeled with Alexa-fluor 488 moieties by a protein labeling kit obtained from Molecular Probes Inc. In brief, a protein solution at a concentration of 2 mg/mL in standard phosphate buffer saline was mixed with 50 µL of sodium bicarbonate solution and the provided vial of Alexa-fluor dye and reacted for 1 h at room temperature. After reaction, the protein-dye conjugate was flowed through a gel separation column (Bio-rad Biogel P-30) for purification. The resulting fluorescently labeled protein solution was then diluted to a concentration of ~10 µM in PBS.

A suspension of the oxidized and cut SWNTs at a concentration of ~0.05 mg/mL was mixed with fluorescently labeled proteins (typical protein concentration ~1 µM) for ~2 h at room temperature prior to characterization (by e.g., atomic force microscopy (AFM) for imaging protein-SWNT conjugates) or cellular incubation for uptake. After this simple mixing step, proteins were found to adsorb non-specifically onto nanotube sidewalls.

Example 11

Protein Binding on Oxidized SWNTs

The combined treatment of refluxing and sonication in nitric acid is known to produce short (50-500 nm) individual or small bundles of SWNTs with oxygen containing groups (e.g., —COOH) along the sidewalls and ends of the tubes (Kam, N. W. S.; Jessop, T. C.; Wender, P. A.; Dai, H. J. *J. Am. Chem. Soc.* 2004, 126, 6850; Chen, J.; Hammon, M. A.; Hu, H.; Chen, Y. S.; Rao, A. M.; Eklund, P. C.; Haddon, R. C. *Science* 1998, 282, 95; Liu, J.; Rinzler, A. G.; Dai, H.; Hafner, J. H.; Bradley, R. K.; Boul, P. J.; Lu, A.; Iverson, T.; Shelimov, K.; Huffman, C. B.; Rodriguez-Macias, F.; Shon, Y.-S.; Lee, T. R.; Colbert, D. T.; Smalley, R. E. *Science* 1998, 280, 1253). These functional groups impart hydrophilicity to the nanotubes and make them stable in aqueous solutions (in pure water and various buffers including PBS and cell culture media) without apparent aggregation in the timescale monitored (1-3 h). In the current work, we found that simple mixing of the oxidized SWNTs with protein solutions led to non-specific binding of proteins to the nanotubes as can be gleaned from AFM studies of various oxidized SWNT samples deposited on $SiO_2$ substrate. Nanotubes could be seen to bear discernible enlargements representing individual proteins displayed along the length of the nanotube. In the case of cytochrome C, the tube was almost continuously coated. Otherwise, a tube appeared to have about 5 molecules of protein adhered thereto (BSA and, SpA). AFM imaging revealed that the average spacing between proteins adsorbed on SWNTs ranged approximately from ~20-100 nm and the loading appeared to be the highest for cyt-c likely due to attractive electrostatic interactions (isoelectric point pI ~9.2 for cyt-c and the oxidized SWNTs were negatively charged). Proteins with pI <7 such as SA and BSA also exhibited affinity for oxidized SWNT sidewalls. We attributed the binding to either electrostatic forces between functional groups on SWNTs and positively charged domains on proteins, and/or hydrophobic interactions since the SWNT sidewalls were not fully oxidized (tens of nanometer between oxygen groups) and contained hydrophobic regions.

After SWNT-protein conjugation, a drop of the solution (~50 µL) was pipetted onto a clean $SiO_2$ substrate and allowed to stand for ~30-45 min. The substrate was then rinsed with copious amount of HPLC grade $H_2O$ and dried by a $N_2$ stream.

AFM images were made of various SWNT samples deposited on $SiO_2$ substrate. (a) Oxidized SWNT prior to conjugation with proteins and after conjugation to 1 µM of (b) Alexa-Fluor 488 BSA, (c) Alexa-Fluor 488 spA and (d) Alexa-Fluor 488 cytochrome C. These images showed uptake of the proteins on to the nanotubes as described above.

Example 12

Incubation of Living Cells in Solutions of Protein-Nanotube Conjugates

Non-adherent HL60 and Jurkat cells were both grown in RPMI-1640 cell culture medium (Invitrogen) supplemented with 10% fetal bovine serum (FBS). Adherent HeLa and NIH-3T3 cells were grown in DMEM cell medium (Invitrogen) supplemented with 10% FBS and 1% penicillin-streptomycin. The cell density for all cell lines used in the incubation was $\sim 3 \times 10^6$ cells/mL.

For incubating HL60 and Jurkat cells in nanotube solutions, 100 µL of the cell suspension was typically mixed with 100 µL of a protein-SWNT conjugate solution at 37° C. for 2-3 h in 5% $CO_2$ atmosphere. The concentration of SWNTs in the incubation solution was typically ~0.05 mg/mL. After incubation, the cells were washed, collected by centrifugation and re-suspended in the cell culture medium twice.

For incubating HeLa and NIH-3T3 cells in nanotube solutions, the cells were seeded into 8-well chambered cover slides ~24 h prior to incubation in a protein-SWNT solution in DMEM cell growth medium. The incubation conditions were the same as the one for non-adherent cells above. Since the cells were adhered to the cover-slide surface, no centrifugation was needed to separate the cells from the incubation solution. The cells were washed by changing the cell medium and then characterized by confocal microscopy imaging.

Example 13

Measurement of Cellular Uptake of Protein-Nanotube Conjugates

For flow cytometry measurements, the cells were analyzed by a Becton-Dickinson FACScan instrument after incubation for 2-3 h in a solution of fluorescently labeled protein-SWNT conjugate. The cell suspension was supplemented with 2% propidium iodide (PI, Fluka chemicals) to stain dead cells. The data presented here represent the mean fluorescence obtained from a population of 10,000 cells. Note that the mean fluorescence reported was a measure of fluorescence of live cells only as cells showing high levels of PI staining were excluded from the analysis.

Cell cytometry data showed that the cells treated with fluorescently labeled SA and SpA significantly absorbed the conjugates.

After incubation in solutions of fluorescently labeled protein-SWNT conjugates, confocal images of cells were recorded with a Zeiss LSM 510 confocal microscope immediately (except for cell viability assay described later) following the incubation in solutions of protein-SWNT conjugates and washing steps. In the case of non-adherent cells, 20 µL of the cell suspension were pipetted onto a glass cover slide before imaging. Adherent cells were imaged directly in chambered cover slides.

Confocal microscopy and flow cytometry characterization of cells after incubation in protein-SWNT (proteins labeled to be green fluorescent) solutions for 2 h was carried out with (a) HL60 cells after incubation in streptavidin SA-SWNTs (b) HL60 cells after incubation in BSA-SWNTs; and (c) HeLa cells after incubation in SA-SWNTs in the presence of the FM 4-64, a red membrane and endocytotic vesicle marker.

Yellow color indicated co-localization of fluorescently labeled green proteins and red FM 4-64. That is, the colors in the images showed that the labeled proteins co-located with the dye that is specific for endocytotic vesicles (namely, dye FM 4-64) HeLa cells were observed after incubation in cytochrome c-SWNTs in the presence of FM 4-64. It could be seen that the cell nucleus (dark circular or oval-shaped regions) appears free of fluorescence with the internalized protein-SWNT conjugates accumulating outside of the nucleus region and outlining parts of the nucleus boundary.

Alexa-fluor 488 (excitation wavelength ~488 nm and emission wavelength ~510 nm) was used. The proteins were conjugated to SWNTs in concentration ranging from 100 nM-1 µM with SWNT concentration of ~0.05 mg/mL. For various non-adherent cells (HL-60 and jurkat) and adherent cell lines (HeLa and NIH-3T3), we found that intracellular internalization of protein-SWNT conjugates was generic for the various proteins investigated by confocal microscopy imaging (data not shown) and flow cytometry (data not shown). Optical confocal microscopy sections (in the Z-direction) of the cells revealed that fluorescence was mainly originated within the cell interior, though cell membrane-surface bound fluorescence of protein-SWNT conjugates was also present. As control experiments, we carried out incubations of cells in solutions that contained fluorescently labeled proteins alone and compared the detected fluorescence level with cells exposed to protein-SWNTs by flow cytometry. The fluorescence level detected for the former was low compared to the latter, suggesting that while proteins in solutions were unable to traverse across cell membranes by themselves, SWNTs were effective in transporting protein cargos inside cells.

The observed internalization of the non-covalently bound proteins via oxidized SWNT transporters was similar to that of streptavidin transported by biotinylated SWNTs for which endocytosis was identified as the internalization pathway (Kam). Endocytosis is a well-known mechanism for a wide range of species traversing cell membranes including large liposomes and nanoparticles, and is an energy-dependent internalization mechanism hindered at low temperatures (Silverstein, S. C.; Steinman, R. M.; Cohn, Z. A. *Annu. Rev. Biochem.* 1977, 46, 669; Vida, T. A.; Emr, S. D. *J. Cell Bio.* 1995, 128, 779; Mukherjee, S.; Ghosh, R. N.; Maxfield, F. R. *Physiol. Rev.* 1997, 77, 759). Indeed, by incubating cells in protein-SWNT conjugates at 4° C., we observed no uptake of the conjugates (FIG. 3), suggesting the endocytosis mechanism for the cellular uptake of protein-nanotube conjugates in experiments performed at 37° C. FIG. 3*c* shows that the percentage of fibroblast cells exhibiting apoptosis (as evidenced by annexia staining) is greatest when cytochrome c is released from the complex.

Additional experimentation may be carried out to address whether the conventional endocytosis mechanism involving clathrin coated pits (Schmid, S. L. *Annu. Rev. Biochem.* 1997, 66, 511) on cellular membranes is involved for the nanotube uptake. We speculate that SWNTs exhibit high binding affinity to certain cell membrane species that facilitate the high efficiency of nanotube binding and subsequent internalization. This binding affinity exists even after protein adsorption on SWNTs since the protein coverage is often incomplete (Kam) and the nanotube/protein complex still exhibits substantial hydrophobicity. The uptake mechanism certainly warrants much future effort and we will present our detailed mechanistic study in a separate publication. Discrepancy in uptake mechanisms for nanotubes, i.e., endocytosis found by us and phagocytosis proposed by Cherukiri, et al., (Cherukiri, P.; Bachilo, S. M.; Litovsky, S. H.; Weisman, R. B. *J. Am. Chem. Soc.* 2004, 126, 15638), versus insertion and diffusion by Pantarotto, et al., and Bianco, et al., (Pantarotto, D.; Briand, J.; Prato, M.; Bianco, A. *Chem. Comm.* 2004, 1, 16; Lu, Q.; Moore, J. M.; Huang, G.; Mount, A. S.; Rao, A. M.; Larcom, L. L.; Ke, P. C. *Nano Lett.* 2004, 4, 2473; Cherukuri, P.; Bachilo, S. M.; Litovsky, S. H.; Weisman, R. B. J. Am. Chem. Soc. 2004, 126, 15638; Bianco, A.; Hoebeke, J.; Godefroy, S.; Chaloin, O.; Pantarotto, D.; Briand, J.-P.; Muller, S.; Prato, M.; Partidos, C. D.; 16 Dec. 2004, W. R. D. *J. Am. Chem. Soc.* 2005, 127, 58) needs to be reconciled.

We note that while binding and intracellular protein transporting by SWNTs appeared general for small to medium sized proteins (molecular weight ≤80 kD), (BSA≈67 Kd) cellular uptake of protein-SWNT conjugates was poor and nearly non-existent for a large protein investigated, i.e., human immunoglobulin (molecular weight≈150 kD). This observation (data not shown) is not understood currently and is likely related to the large size of the antibody cargo, which may have caused inefficient loading of hIgG on SWNTs due to the large size mismatch (≈7-8 nm for hIgG; ~1.5 nm in diameter for SWNT) or inefficient endocytosis due to the large conjugates. The issue of binding and transporting of large proteins and antibodies with SWNTs is open for further investigation.

However, based on the experimental results to date, it is expected that proteins up to 80 kD may be delivered to living cells non-covalently coupled to carbon nanotubes without modifying the exemplified techniques.

Example 14

Cell Proliferation MTS Assay

Biocompatibility is a major concern when introducing any foreign substances inside living systems. Thus far, several groups have reported that relatively pure, well solubilized short carbon nanotubes appear nontoxic once internalized into mammalian cells without apparent adverse effects to cell viability (Kam, Pantarotto, Lu, Cherukuri, Bianco). In the current work, we further assessed the biocompatibility of carbon nanotubes by monitoring cell proliferation.

After incubation with the SWNT-streptavidin conjugate (unlabeled), HL-60 cells were washed and resuspended in RPMI media. The cells were plated in a 6-well plate at a density of ~8×10$^3$ cells/well. At 24 h interval, Celltiter96 reagent (Promega) was added to one of the wells and allowed to incubate for ~2-3 h at 37° C. and 5% CO$_2$. The CellTiter 96 assay uses the tetrazolium compound (3-(4,5-dimethylthiazol-2-yl)-5-(3-carboxymethoxyphenyl)-2-(4-sulfophenyl)-2H-tetrazolium, inner salt; MTS) and the electron-coupling reagent, phenazine methosulfate (PMS). MTS is chemically reduced by cells into formazan, which is soluble in tissue culture medium. The measurement of the absorbance of the formazan can be carried out at 490 nm. The assay measures dehydrogenase enzyme activity found in metabolically active cells.

We used the CellTiter 96 MTS assay (Promega) to examine the proliferation of HL60 cells following exposure to SWNT-protein conjugates. The CellTiter 96 assay uses the tetrazolium compound (3-(4,5-dimethylthiazol-2-yl)-5-(3-carboxymethoxyphenyl)-2-(4-sulfophenyl)-2H-tetrazolium, inner salt; MTS) and the electron-coupling reagent, phenazine methosulfate (PMS). MTS is chemically reduced by cells into formazan, which is soluble in tissue culture medium. The absorbance of the formazan salt can be measured at 490 nm and correlates to the number of cells in the suspension. The absorbance from the cells incubated with the SWNT-protein conjugates was measured over a period of 5 days in parallel with control cells never exposed to any nanotubes. The absorbance detected by a UV-VIS spectrophotometer was very similar for cells with and without exposure to SWNTs over the 5-day monitoring period. This result suggest that cell proliferation and cell viability was unaffected by the internalized carbon nanotubes.

Cells were incubated with SWNT-SA conjugate (without fluorescent label) for 2 hrs. After incubation, cells are washed, collected and resuspended in cell media. Confocal images of HeLa cells taken (a) 24 hrs and (b) 48 hrs after incubation. The cells were plated at a cell density of 8×10$^3$ cells/well and returned to a CO$_2$ incubator at 37° C. and 5% CO$_2$. At 24 hr interval after the initial SWNT incubation, CellTiter96 reagent was added to the cell suspension, and allowed to incubate for 2 hrs at 37° C. The absorbance is then taken at 490 nm. The proliferation of the cells incubated with SWNT was monitored for a period of up to 5 days after initial exposure to SWNT and does not show any deviation from the proliferation of untreated cells.

Example 15

Endosome Release of Cytochrome C by pH Change Resulting from Chloroquine Administration To investigate the effect of endosomal release on the efficiency of apoptosis induction by cyt-c transported by SWNTs, we carried out incubations of cells in cyt-c-SWNT with and without the presence of chloroquine. Higher degrees of apoptosis were consistently observed for cells treated with cyt-c-SWNT in the presence of chloroquine (FIG. 3*c*) as attributed to the more efficient endosomal releasing of proteins. Note that the apoptosis results presented here were reproduced at least three times in independent experimental runs. Also, unless otherwise stated, chloroquine was used in all incubations including control experiments for fair comparisons with the positive control (cyt-c-SWNT+chloroquine incubation). Taken together, our data suggested that the cytochrome c bound and transported inside cells by SWNT carriers remained biologically active for apoptosis induction. It was unclear however, whether the cytochrome c functionality was obtained after detaching from the SWNT sidewalls or with the proteins bound to nanotubes. As observed previously, SWNT-protein conjugates, once internalized inside mammalian cells were colocalized with a red endocytosis endosome marker FM 4-64 corresponding to the containment of internalized species in endosomal lipid vesicle compartments (specifically labeled by red FM-64). Consistent with this was the observed punctuate fluorescence (FIG. 2, first panel) inside cells due to endosomal confinement of the internalized species. The endocytosis pathway can be illustratively described as the engulfment of the cell membrane and formation of a lipid vesicle around the species to be internalized (Silverstein, Vida, Mukherjee). Once inside the cells, the endosomes could fuse with the cell lysosomes, which may lead to later degradation of the internalized species in the lysosomes. To avoid the fate of lysosome degradation, it is important to trigger endosomal release of the internalized molecules into the cell cytoplasm. This will then open up the possibility of obtaining biological functionality for the internalized cargo molecules. Note that green fluorescence (proteins) non-overlapping with FM 4-64 markers were sometimes observed (FIG. 2), suggesting certain internalized species might have been released from the endosome via an intentional mechanism.

Various approaches have been suggested in the past to actively initiate endosomal release of endocytosed species including complexation of the cargo molecules with pH sensitive polymers or highly amine-rich moieties Lackey, C. A.; Murthy, N.; Press, O. W.; Tirrell, D. A.; Hoffman, A. S.; Stayton, P. S. Bioconj. Chem. 1999, 10, 401; Cho, Y. W.; Kim, J. D.; Park, K. J. Pharm. Pharmacol. 2003, 55, 721). These methods make use of the pH difference across the endosome membrane and the pH response of the polymers or amines. For SWNT transporters, similar complexation schemes can be developed to afford nanotube transporters containing an endosome-releasing agent. While such an effort warrants detailed investigations separately from the current work, we describe here the release of internalized protein-SWNT conjugates from the endosomal compartments by adding chloroquine to cell medium during incubation of cells in protein-SWNT conjugates. Chloroquine is a membrane permeable base that has been shown to localize inside endosomes and cause an increase in pH (Maxfield, F. R. J. Cell Biol. 1982, 95, 676). The resulting osmotic pressure can lead to swelling of the endosomal compartments and eventual rupture (Ogris, M.; Steinlein, P.; Kursa, M.; Mechtler, K.; Kircheis, R.; Wagner, E. Gene Ther. 1998, 5, 1425).

In experiments carried out with and without chloroquine, we noticed a difference in the distribution of the detected fluorescence inside the cells. In the absence of chloroquine, discrete punctate fluorescence spots were observed within the cells (FIG. 2). In contrast, when cells were simultaneously exposed to protein-SWNT conjugates and 100 µM chloroquine, fluorescence signals inside the cells appeared to be diffuse and uniform, due to redistributed conjugates over the entire cell cytoplasm after endosome releasing. FIG. 2 (a) Cells are incubated with (a) SWNT-CytC conjugate and (b) SWNT-CytC+100 µM of chloroquine at 37° C. and 5% $CO_2$ Confocal images are taken immediately after incubation and washing. Confocal images indicating the release of the SWNT-protein conjugate from the endosome, overall green color across the cell in (b) vs. green individualized spots inside the cells in (a).

Example 16

Apoptosis

We use Annexin V labeled with fluorescein isothiocyanate (Molecular Probes) as an early stage apoptosis marker. One of the earliest indications of apoptosis is the translocation of the membrane phospholipid phosphatidylserine (PS) from the inner to the outer leaflet of the plasma membrane. Once exposed to the extracellular environment, binding sites on PS become available for Annexin V, a ~35 kDa $Ca^{2+}$-dependent, phospholipid binding protein with a high affinity for PS (Pigault, C.; Follenius-Wund, A.; Schmutz, M.; Freyssinet, J.; Brisson, A. J. Mol. Biol. 1994, 236, 199) (also see Sigma Technical Bulletin number MB-390). In this study, NIH 3T3 cells were plated and incubated with SWNT-cytochrome c as described above. After incubation, the cells were washed, trypsinized to detach them from the plate surface and washed with phosphate buffer saline. Annexin V-FITC was added to the cell suspension in the presence of the binding buffer and allowed to react for 20 min at room temperature. The cells were co-stained with propidium iodide and immediately analyzed by flow cell cytometry. Apoptosis data in FIG. 3 were for cells free of PI-staining recorded ~4-5 h after exposure to chloroquine with or without (for control) cyt c-SWNT conjugates.

We chose cyt-c for this exploration due to the high degree of loading of cyc-c on SWNTs as shown by AFM) and high efficiency of endocytosis of the cyt-c/SWNT conjugates. Cyt-c is the smallest protein in the current work with a molecular weight of 12 kD and has the highest pI of ~9.2 to afford a high degree of binding onto the negatively charged oxidized SWNTs. It has been suggested that cells during apoptosis or programmed cell death may release cytochrome c from mitochondria (Zhivotovsky, B.; Orrenius, S.; Brustugun, O. T.; Doskeland, S. O. Nature 1998, 391, 449; Cai, J.; Yang, J.; Jones, D. P. Biochim. et Biophys. Acta 1998, 1366, 139). When microinjected, cytochrome c has been shown to induce or activate apoptosis by bypassing the need for release of cytochrome c from mitochondria (Zhivotovsky). Through interaction with apoptotic protease activating factors (Apaf), cyt-c in the cytosol is believed to initiate the activation cascade of caspases that leads to cell death (Cai).

HeLa (human cervix carcinoma) and NIH-3T3 cell lines, shown previously to undergo cyt-c-induced apoptosis were investigated in this study for intracellular transporting of cyt-c with SWNTs and for apoptosis assay (Cai). Unlike the proteins used for other uptake experiments, cyt-c used for binding to SWNTs and transported inside cells for apoptosis assay were free of any fluorescence label. After incubation of cells in the cyt-c-SWNT conjugates, apoptosis was analyzed using fluorescently (FITC) labeled Annexin V. Annexin V-FITC is an efficient marker for early stage apoptosis as it binds specifically to the exposed phospholipid phosphatidylserine (PS) translocated from the inner to the outer leaflet of the plasma membrane during apoptosis. Once exposed to the extracellular environment, binding sites on PS become available for Annexin V, a ~35 kDa $Ca^{2+}$-dependent, phospholipid binding.

For NIH-3T3 cells incubated with cyt-c alone and cyt-c-SWNT conjugates, we analyzed the degree of Annexin V staining by both confocal microscopy. The results are shown in FIG. 3.

FIG. 3 illustrates apoptosis induction by cytochrome c cargos transported inside cells by SWNTs. FIG. 3 (a) is a confocal image of NIH-3T3 cells after 3 h incubation in 50 µM of cytochrome c alone (no SWNT present) and 20 min staining by Annexin V-FITC (green fluorescent). (b) Images of cells after incubation in 50 µM cytochrome c-SWNTs in the presence of 100 µM chloroquine and after Annexin V-FITC staining. (c) Cell cytometry data of the percentages of cells undergoing early stage apoptosis (as stained by Annexin V-FITC) after exposure to 100 µM of chloroquine only (labeled 'untreated'), SWNT+100 µM of chloroquine, 10 µM of cyt-c+100 µM chloroquine, 10 µM of cyt-c-SWNT+100 µM chloroquine and cyt c-SWNT without chloroquine. The inset shows a representative confocal image of the blebbing of the cellular membrane (stained by Annexin V-FITC) as the cell undergoes apoptosis. Note that PI co-staining was used and all data shown here excluded PI-positive cells and are recorded ~4-5 h after exposure to chloroquine. The level of PI staining for all cells here was a normal ~4-6% out of ~10,000.

In summary, we observed significantly higher percentages of apoptosed cells incubated with cyt-c-SWNT conjugates than those incubated with cyt-c alone (FIG. 3a vs. 3b; also see FIG. 3c). We also encountered apoptotic cells exhibiting blebbing of the cellular membrane stained by Annexin V-FITC (FIG. 3c inset), a known phenomenon for cells undergoing apoptosis.

Examples 17-26

Protein and DNA Conjugation and Delivery Via Non-Covalent Binding with PEG-Phospholipids These examples describe experiments with linking compounds that have an aliphatic group (lipid) linked to a soluble polymer (PEG) and further covalently linked to a protein. The linkage could also be directly to a poorly absorbed drug. The PEG-PL complex is non-covalently bound to the nanotubes through hydrophobic interaction between the aliphatic lipid and the hydrophobic surface of the nanotubes. It is not necessary to functionalize the nanotubes in this case.

Introduction

Non-covalent functionalization of SWNTs has also been accomplished by strong adsorption of phospholipids grafted with polyethylene glycol (PEG) chains. Compared to other surfactants (e.g., sodium dodecyl sulfate, SDS), PEG-phospholipids impart higher stability to the SWNT solution against agglomeration due to rinsing, aging, heating to high temperatures and soaking in highly concentrated salt solutions for extended periods of time. Also, PEG-PL surfactants provide the availability of PEG-PLs with various reactive groups (e.g., $NH_2$-PEG-PL) that allow facile conjugation of proteins and other molecules. This opens up a venue to water soluble SWNTs with a wide range of interesting molecules attached to PEG-PL coated nanotubes. The excellent stability of the PEG-PL solubilized SWNTs in physiological buffers are demonstrated herein in living cells. We notice internalization of PEG-PL functionalized SWNTs into a mammalian cell line via endocytosis, and the nanotubes appear non-toxic. Future experimentation is expected to further demonstrate the biocompatibility and toxicity effects of nanotubes with attached desired ligands or drugs for potential targeting or delivery applications with high specificity.

Figure 4:
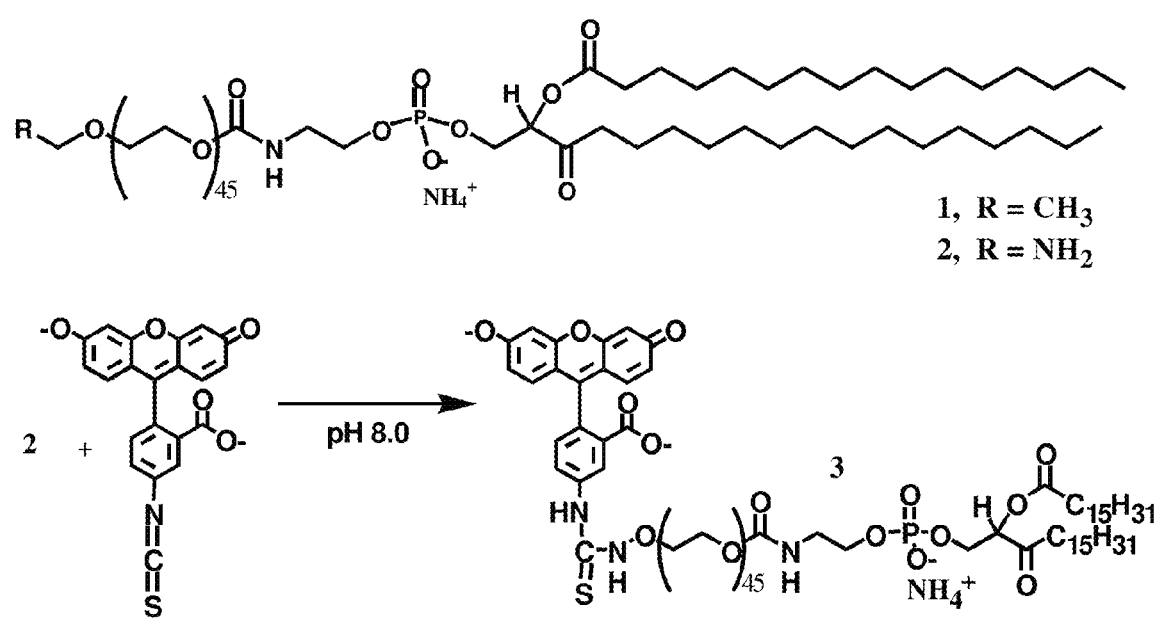
FIG. 4 is an illustration of a reaction scheme showing two PEG-PL molecules (1 & 2) and conjugation of fluorescein isothiocyanate (FITC) (emission 510) to 2.
Figure 5:
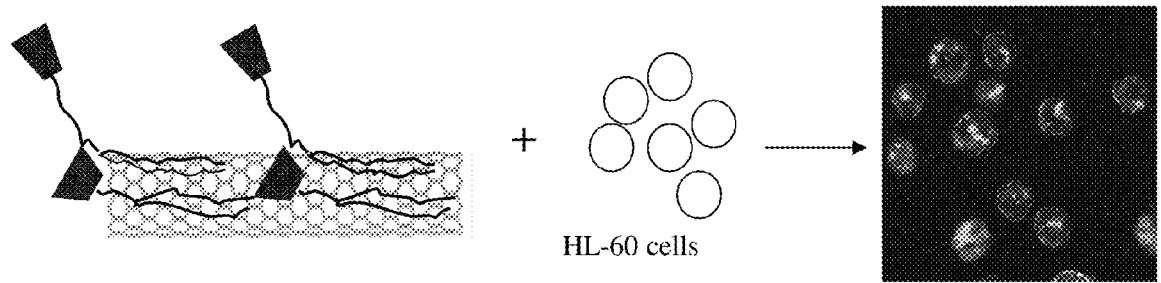
FIG. 5 is a schematic drawing of the nanotubes of FIG. 4 having phospholipids and FITC coupled thereto and being taken up by HL-60 cells.

Referring to FIG. 4, discussed below, various proteins may be substituted for the R group shown. These proteins may have the characteristics described above. That is, R represents the active agent to be delivered, e.g., protein, polynucleotide, or other agent poorly taken up by target cells. Thus, FIG. 4 represents R-PEG-PL, where PEG is polyethylene glycol and PL is a polar lipid, preferably a phospholipid. The lipid portion adsorbs onto a nanoparticle, e.g., SWNT, MWNT, carbon black particle, or polystyrene bead. The linkage of R may further comprise a cleavable linkage, discussed below in connection with FIG. 7.

Compared to other surfactants (e.g., sodium dodecyl sulfate, SDS), PEG-PL impart higher stability to the SWNT solution against agglomeration during rinsing, aging, heating to high temperatures (80° C.) and soaking in highly concentrated salt solutions (up to 1M NaCl) for extended periods of time (up to 48 h). The availability of PEG-PLs with various reactive groups (e.g., NH2-PEG-PL) allows for facile conjugation of other molecules. This opens up a venue to water soluble SWNTs with a wide range of interesting molecules attached to PEG-PL coated nanotubes. We observed a certain degree of internalization of PEG-PL functionalized SWNTs into a mammalian cell line via endocytosis and the nanotubes appear non-toxic in the time studied. Importantly, PEG-PL is non-toxic to cells whereas SDS and many other types of surfactants are.

Example 17

Typical Procedure for Solubilizing SWNTs with PEG-Phospholipids 1 & 2 (FIG. 4)

Carbon nanotubes made by laser ablation or high-pressure carbon monoxide (HiPCO) was added to 0.1% (w/w) aqueous solution of the PEG-phospholipids such that final concentration of nanotubes in the solution is 0.1 mg/mL. The solution was sonicated for 1 h, and then filtered through a 0.1 μm pore-sized polycarbonate membrane (Whatman) to remove excess phospholipids. The resulting black film formed on the membrane is resuspended in the desired solvent ($H_2O$ or buffer) by sonication (5-10 m). The volume of solvent used for resuspension can be adjusted to obtain the desired nanotube concentration.

SWNTs produced by laser ablation and high pressure CO (Hipco) were used in this work and similar results were obtained with the two materials. The nanotubes were added to a 0.1% (w/w) aqueous solution of 1,2-dipalmitoyl-sn-glycero-3 phosphoethanolamine-N-[methoxy(polyethylene glycol)-2000] (1, PEG-PE) or of the amine-terminated 1,2-Distearoyl-sn-Glycero-3-Phosphoethanolamine-N—[Amino(Polyethylene Glycol)2000] (2, NH2-PEG-PE) and the mixture (nanotubes concentration ~0.05 to 0.5 mg/mL) was sonicated for 1 h. Excess phospholipids in the solution were then removed by filtration and the PEG-PL coated nanotubes were re-dispersed in water by sonication for 5-10 m. The resulting nanotube solution was highly homogeneous and stable.

This was shown as follows: Aqueous solutions of 0.05 mg/ml SWNTs were observed after (a) exposure to 0.2 M phosphate buffers at pH 7.0 for 48 h and (b) heating to 80° C. for 24 h. (I)-(III): Solutions with 1% of tween-20, Gum-Arabic and SDS respectively. (IV) and (V): solutions with 0.1% of 1 and 2 respectively with excess lipids removed. (IV) and (V) are the only ones stable against agglomeration in both the high temperature and salt processes.

Example 18

Alternative Conjugation Method Using Disulfide Linkages

This functionalization scheme involves the use of phospholipids as anchors on SWNTs and attachment of biological molecules onto the phospholipids functionalized SWNT via a disulfide linkage, as shown in FIG. 6. The disulfide linkage is desirable for our endocytosed cargo-SWNT since in-vitro enzymatic cleavage of disulfide bonds is well known and can be exploited for cargo releasing from SWNT transporters. With the incorporation of disulfide linkage, we obtain highly water-soluble SWNT-biomolecule conjugates and attain release and delivery of an oligonucleotide cargo from the nanotube transporter. We find that the DNA oligos thus released can reach inside the cell nucleus, and expect that the same results would be obtained with proteins.

Single-walled carbon nanotubes (SWNT) made from the Hipco process were treated by sonication and acid reflux as described previously to afford short (~200 nm) water soluble nanotubes containing acidic surface groups Fluorescently labeled BSA in a concentration range of 100 nM-1 μM was then mixed with the oxidized nanotubes for 1-2 h. The proteins were found to non-specifically bind to the nanotubes to form protein-SWNT conjugates.

SWNTs made from the Hipco process was sonicated in a solution of a 15-mer Cy3 fluorescently labeled oligonucleotides (SEQ ID NO: 1) (CATTCCGAGTGTCCA-Cy3) for ~30 min to 1 h (DNA concentration ~2-10 μM). The resulting suspension was centrifuged at 24,000 g for ~6 h to remove large impurities in the sample. The sonication/centrifugation process was repeated twice. The final decanted solution contained mostly individual SWNTs (50-200 nm in length, tube diameter ~1 nm as revealed by AFM topography height measurements) wrapped by DNA oligos.

Two cell lines, human promyelomonocytic HL60 cells and cervical cancer HeLa cells were used in the current work. HL60 were cultured in RPMI medium supplemented with 10% fetal bovine serum (FBS), while HeLa cells were cultured in DMEM medium supplemented with 10% FBS and 1% penicillin-streptomycin. The cells were suspended in phosphate buffered saline (PBS), mixed with a SWNT conjugate and incubated for 1-3 h at 37° C., except for the low temperature incubations. The concentration of SWNTs in the incubation solution was typically ~2.5 mg/L as measured by UV-vis-NIR absorption spectrum, and the cell density was ~$2\times10^5$ cells/well. Adherent HeLa cells were either trypsinized to detach from the Petri dishes to form a suspension or were seeded overnight in chambered cover-slides.

SWNT were sonicated in a solution of 1,2-Distearoyl-sn-Glycero-3-Phosphoethanolamine-N4-Amino(Polyethylene Glycol)2000] (Avanti Polar Lipids). This phospholipids molecule contained a polyethylene glycol chain (45 units) and was terminated with an amine group (PEG-PL-$NH_2$). The typical PEG-PL-$NH_2$ concentration ranged between 0.1-1 mg/mL). The suspension was filtered through a membrane filter (Whatman, pore size 100 nm) to remove excess PEG-PL, rinsed thoroughly with $H_2O$ and re-suspended in either $H_2O$ or buffer. The suspension was centrifuged as described above to remove impurities and large nanotubes bundles.

2.5 mg of Sulfosuccinimidyl 6-(3'-[2-pyridyldithio]-propionamido)hexanoate (sulfo-LC-SPDP, Pierce) was added to a solution of SWNTs functionalized with PEG-PL-$NH_2$ in 0.1M phosphate buffer (supplemented with 0.15M NaCl. pH 7.4). The mixture was allowed to react at room temperature for 1 h and then SH-DNA-cy3 was added such that final DNA concentration was 2 μM. The mixture was allowed to react overnight. After reaction, the conjugate was centrifuged through a centrifugal filter with molecular weight cutoff of 100 kD (Millipore) for 5 min twice to remove excess DNA. The nanotube conjugates were then re-suspended in $H_2O$ for further experiments. A solution of DNA-SS-SWNT conjugates (in a 10 mM phosphate buffer, pH 7.0) was exposed to dithiothreol (DTT, 10 mM, Aldrich) and allowed to react for 2 h at room temperature. Following the reaction, the mixture was filtered twice through a membrane filter (100 nm pore size) and re-suspended in $H_2O$. A control solution of DNA-SS-SWNT not exposed to DTT was also filtered twice and re-suspended in $H_2O$ prior to fluorescence measurement with a Fluorolog 3 fluorimeter (excitation=550 nm and emission=560 nm).

The third SWNT conjugate (DNA-SS-SWNT) used in this study was made in two steps. (FIG. 4). First, as-grown SWNTs were sonicated in a solution of phospholipids molecules grafted with a polyethylene glycol (PEG) chain with a terminal amine functional group (PL-PEG-$NH_2$) to afford a highly stable aqueous dispersion of SWNT. The amine functionality imparted onto the nanotubes surface was then reacted to a heterobifunctional cross-linker based on an N-succinimidyl 3-(2-pyridyldithio) propionate molecule (sulfo-LC-SPDP). The cross-linker allowed the formation of a disulfide bond between an amine containing molecule and a sulfhydryl containing species (in our current case, the sulfhydryl containing molecules was a 15-mer oligonucleotide with a 5' thiol group and the sequence of the oligo was (SH-$(CH_2)_6$CATTCCGAGTGTCCA-Cy3) (SEQ ID NO: 2). Due to sonication, nanotubes in all of our conjugates were short (~200 nm), individualized or small bundles of nanotubes as characterized by atomic force microscopy.

Upon incubation of non-adherent HL60 and adherent HeLa cells in solutions of SWNT-protein, SWNT-DNA and SWNT-SS-DNA, we observed cellular internalization of these conjugates by fluorescence confocal microscopy. Both the protein and DNA molecules were labeled with a fluorescent tag (by either Cy3 or Alexa Fluor 488) to allow for confocal fluorescence imaging and flow cytometry analysis.

Endocytosis is an energy-dependent intracellular uptake process blocked at low temperature (4° C.) and in ATP depleted environments. We carried out incubations of protein-SWNT and DNA-SWNT with HL60 and HeLa cells at 4° C. and with cells pretreated with $NaN_3$. The latter has been shown to block ATP production inside cells, thus hindering uptake by the endocytotic pathway. The respective level of fluorescence observed in the cells after low temperature incubation and ATP depletion was considerably lower, indicating endocytosis as the general internalization mechanism for the SWNT conjugates.

The disulfide bond is specifically chosen to exploit disulfide bond cleavage by intracellular enzymes, a process that has been shown to be favored by the acidic pH environment of endosomes and lysosomes. The reduction of the disulfide linkage thus leads to the releasing of the cargos from nanotubes. Our functionalization scheme utilizes phospholipids (PL) molecules grafted with polyethylene glycol chains (PEG-PL) for non-covalent binding to SWNT sidewalls and serving as anchor point for subsequent conjugation steps. PEG-PL molecules are commercially available with various functional groups at the termini of PEG moieties. The double alkyl chains on the PL bind to the nanotube sidewalls via van der Waals and hydrophobic interactions in aqueous solution, while the hydrophilic PEG (45 units) moieties can afford high aqueous stability to the SWNT-PL-PEG complex. For SWNTs functionalized by PL-PEG-$NH_2$, we used a heterobifunctional cross-linker (sulfo-LC-SPDP) to conjugate a thiolated-oligo to the complex. This led to a water soluble and stable SWNT-SS-DNA conjugate.

Cleavage of the disulfide bond released DNA from the nanotube carrier. This result was in stark contrast with that obtained with DNA-SWNT conjugates without a disulfide linkage for enzymatic cleavage and releasing. In the latter case, red fluorescence corresponding to the DNA molecules appeared to be constrained outside of the cell nucleus without apparent nuclear translocation. Apparently, without releasing of DNA from SWNT transporters, the SWNT-DNA conjugates accumulated in the peri-nuclear region and were unable to penetrate through the nuclear membrane and diffuse into the cell nucleus.

To characterize and further verify the disulfide linkage, we added dithiothreitol (DTT) to a solution of DNA-SS-SWNT ex-vitro. DTT, also known as Cleland's reagent is commonly used to reduce disulfide linkage into free sulfhydryls. We were able to observe DTT cleavage of the disulfide bond by monitoring fluorescence of the Cy3 labeled DNA on the SWNT conjugates. The fluorescence intensity of the Cy3 label (excitation=550 nm and emission=565 nm) was measured for DNA-SS-SWNT conjugates with and without treatment with DTT and after filtration through a membrane (100 nm pore size) multiple times to remove any free Cy3-DNA molecules in the solutions. After DTT treatment and filtration of Cy3-DNA, a dramatic decrease in fluorescence was observed for the DNA-SS-SWNT conjugates. This confirmed the presence of disulfide linkage in the initial SWNT conjugates and successful cleavage by DTT. To our knowledge, this was the first time that water-soluble SWNT-SS-biomolecule conjugates were obtained. The utility of such conjugates was illustrated here by nuclear delivery of oligonucleotides by SWNT transporters.

Example 19

(Comparative Example): Procedure for Solubilizing SWNTs with Other Surfactants

CNTs are sonicated for 1 h in 2% w/w aqueous solutions of SDS, tween-20 and Gum-Arabic (all from Aldrich). The concentration of CNT in the solution is 0.1 mg/mL. A one-fold dilution was then carried out with $H_2O$ or buffer to obtain samples for the heat and salt stability studies, respectively.

Among nanotubes solubilized by tween-20.4 SDS6 and Gum Arabic, 7 the PEG-PL solubilized SWNTs are the only ones that did not precipitate out under both high temperature (80° C.) and high salt (0.2 M) conditions. Note that the weight concentration of PEG-PL initially used to disperse nanotubes was 10-fold lower than other surfactants. Further, unlike the PEG-PL case, excess surfactants were kept in the SDS, tween-20 and Gum Arabic stabilized nanotube solutions. The unmatched stability of PEG-PL solubilized SWNTs suggests strong binding of the phospholipids on the nanotube sidewalls, most likely via the two alkyl chains on the lipid. The long PEG chain (MW 2000) also appears to be important in imparting high hydrophilicity to the SWNTs, since nanotubes solubilized by phospholipids with shorter PEG chains (MW 750) are less stable under high temperature and salt conditions (data not shown).

Example 20

Conjugation of Fluorescein Isothiocyanate (FTIC) to $NH_2$-PEG-Phospholipids (3) in FIG. 4

Various molecules can be readily attached to NH2-PEG-PLs and the resulting conjugates can be used to solubilize SWNTs. A wide range of functionalities can therefore be imparted to nanotubes through the attached molecules. As an example, fluorescence signals from cell interiors were observed by confocal microscopy. Images (data not shown) illustrate the fluorescence of a solution of SWNTs functionalized by NH2-PEG-PE conjugated with fluorescein isothiocyanate (FTIC, see FIG. 4). Water-soluble SWNTs with fluorescent labels in the visible regime are thus obtained.

3 mg of $NH_2$-PEG-PE (Avanti Polar Lipids) was dissolved in 1.5 mL of 0.1 M carbonate buffer solution (pH 8.0). To this solution 100 µL of 13 mM solution of fluorescein isothiocyanate (FTIC) in DMSO (Aldrich) was added. The mixture was allowed to react overnight at room temperature and protected from light. Purification by gel chromatography was achieved by loading 1 mL of the solution to a Sephadex G-25 column (Aldrich). As elution solvent ($H_2O$) was flown through the column, the formation of two separate yellow bands was observed. The fractions were collected and the absorbance of various fractions was measured at 488 nm using a HP-8453 spectrophotometer. Two distinct and separated peaks were observed from the elution profile (data not shown); fractions from the first elution peak were pooled as they were attributed to the higher molecular weight fluorescent-PL conjugate (also confirmed by excitation and emission spectra), and subsequently used for solubilization of nanotubes. The second peak was assigned to the lower molecular weight, unconjugated FTIC, and confirmed by that these fractions failed to solubilize CNTs, thus indicating very low concentrations or absence of phospholipids in these fractions.

FTIC-PEG-PE conjugate was purified by gel chromatography, using a Sephadex G-25 column. The absorbance of the different fractions was recorded at 488 nm. The first peak was FTIC-PEG-PE conjugate as higher MW molecules are expected to elute first; and the second peak is attributed to any unreacted FTIC in the solution.

Example 21

Removal of Impurity Particulates and Microscopy Characterization of Materials in the Resulting Nanotube Solutions After solubilization of SWNTs with PEG-phospholipids 1, 2 or 3 (as described in Examples 21 and 23), the nanotube solution was centrifuged at 7000 rpm for 5 min. The supernatant was collected and filtered through a polycarbonate membrane (100 nm pore size) to remove additional impurities <100 nm in size and then re-suspended in water. Materials in the resulting nanotube solution were then deposited on a $SiO_2$ substrate modified with 3-aminopropyltriethoxysilane (APTES) and imaged by atomic force microscopy (AFM). AFM images (data not shown) reveal that the deposited materials from the solution onto the substrates were mostly isolated nanotubes with diameters on the order of ~2 nm and lengths ranging from 35-500 nm.

Example 22

Incubation of HL-60 Cells in Solutions of PEG-PL Functionalized Nanotubes

The stability of our phospholipids functionalized SWNTs in physiological buffers allowed in-vitro examination of the interactions between nanotubes and HL-60 cells, a promyelocitic cell line. The HL-60 cells were incubated at 37° C. for 90 min in a solution (5% CO2 in RPMI-1640 medium supplemented with 10% fetal bovine serum) of FTIC-PEG-PE (3) functionalized nanotubes (tubes concentration ~0.025 mg/mL). The nanotube solution remained dispersed after incubation without agglomeration. Note that prior to incubation, large metal catalyst particles in the raw material were removed by centrifugation. The resulting solution consisted of mainly isolated SWNTs with diameter ~1-2 nm and length ~35-500 nm as revealed by microscopy imaging of the materials.

HL-60 cells (~3×10$^6$/ml) were washed and suspended in 100 µL of RPMI 1640 cell media supplemented with 10% Fetal Bovine Serum (Invitrogen Corporation). 100 µL of the SWNT-fluorescent phospholipids solution (SWNT concentration ~0.05 mg/ml) was then added to the cells. The resulting cell suspension was incubated for 90 min at 37° C. and 5% $CO_2$ atmosphere. After incubation, the cells were rinsed twice and resuspended in the RPMI medium. The cells were deposited onto a cover glass and analyzed by Zeiss LSM 510 confocal microscope.

The cells were collected by centrifugation, washed and resuspended and imaged with a Zeiss LSM 510 confocal microscope. Fluorescence was detected from the cells, and z-slice images revealed fluorescence signals originating from the interior of the cells rather than from the cell surfaces. This suggests that though the majority of the FTIC-PEG-PE functionalized nanotubes remained stable in solution (i.e., the functionalized nanotubes were mostly inert) when mixed with cells, a detectable amount was internalized into the cells from the solution. In control experiments, we detected no fluorescence from the cell interiors after incubation in FTIC-PEC-PE solutions without nanotubes.

Example 23

Cell Viability Study with PEG-Phospholipids

Potential toxicity to the cells due to exposure to PEG-PL functionalized SWNTs was investigated by imaging the cells 24 h post incubation and staining the dead cells by propidium iodide. We observed that the PL-functionalized SWNTs did not reduce HL-60 cell viability when compared to untreated cells. The experiments below also identify the internalization mechanism for the nanotubes and found that endocytosis is a likely pathway. This was based on the observation that for incubations carried out at 4° C. at which endocytotic pathway should be blocked. No apparent fluorescence was detected inside the cells.

Similar experiments were attempted with SWNTs coated with other surfactants including fluorescently tagged Tween-20. However, these nanotubes were unstable in physiological buffers and precipitated during incubation with the HL-60 cells. Upon centrifugation to collect the cells, we observed that the nanotubes mixed and aggregated with the cell pellet. It is therefore difficult to assess how nanotubes interact with cells when significant aggregation of nanotubes occurs in the solution. Cells tended to die when exposed to Tween-20.

HL-60 cells were incubated and then washed to remove excess nanotubes, as described above. The cells were then placed into the incubator for an additional 24 h with the RPMI medium. The cells were then examined through a confocal microscope, after being stained with 2% (v/v) of propidium iodide (Biochemika), a common stain for dead cells. Control experiments were carried out for cells without exposure to nanotubes. Observation in the confocal microscope showed that the number of dead cells (with red stain) observed in both cases is similar, suggesting that incubation of cells in a solution of PEG-PL functionalized nanotubes does not cause cell death.

The confocal images (not shown) of HL-60 cells were obtained (a) untreated (b) treated with FTIC-PEG-PE modified CNTs for 90 min at 37° C. Cells were washed and allowed to incubate for an additional 24 h prior to confocal analysis. Propidium iodide is added to the suspension in order to stain for dead cells (red cells in the images).

To further elucidate the uptake mechanism, cells were incubated with fluorescein-phospholipids functionalized SWNTs for 90 min as described before except that the temperature was controlled at 4° C. instead of 37° C. The cells were then imaged by confocal microscopy. The images (data not shown) show fluorescence detected around the rims of the cells, and none from the cell interior (from the z-slice images). This indicates that FTIC-PEG-PE functionalized SWNTs adsorbed onto the outer surfaces of the cells to a certain extent, but no internalization has occurred at this temperature due to the blocking of the endocytosis pathway.

Examples 24-27

Delivery of SiRNA-Nanotubes to Human T Cells and Primary Cells

RNA interference (RNAi) is a mechanism of post-transcriptional gene silencing introduced by small interfering RNA (siRNA). The most widely accepted model of RNAi involves two stages: 1) an initiation step and 2) an effector step. The initiation step consists of the injection of long double-stranded RNA molecules into the cell (via injection, electroporation, lipofection, etc.). The double-stranded RNA (dsRNA) is then cleaved into short RNA duplexes (21-23 nucleotides) by the DICER enzyme (RNase III family of dsRNA-specific ribonucleases). In some cases, the dsRNA may induce a non-specific interferon response resulting in non-specific gene silencing. To prevent or minimize this non-specific response, small interfering RNAs (siRNAs) can be injected directly into the cell. In order to render the siRNAs functional, cellular kinase proteins are used to add a 5' phosphate group to the RNA duplex, producing a 19-21 base-pair siRNA duplex possessing a 2 nucleotide, 3' overhang.

siRNAs have attracted attention as a new class of therapeutic agents that can potentially function against a number of diseases, including cancer and AIDS. It is believed that by silencing the expression of HIV specific receptors (CD4) or co-receptors (CCR5 and CXCR4), the entry of HIV virus into host human T-cells can be blocked and HIV infection can be inhibited. However, efficient siRNA delivery is critical to the RNAi potency. Human T-cells are known to be hard to transfect by normal commercial cationic liposome or polymer based transfection agents, as are primary cells and certain cell lines, such as those of leukocytes (T cells), neuronal cells, embryonic stem cells, and dendritic cells. Currently, only two effective transfection methods exist for human T-cells, electroporation and viral based transfection, but both of which have their limitations. The electroporation method needs a special device to apply a voltage in the cell medium, which is impossible to be transferred to in vivo or clinical applications. Notable damage will be caused to cells as well. Viral based transfection has been proved to be an efficient siRNA transfection method used for in vitro as well as in vivo applications, but further application is seriously limited by the safety issue of the viral vectors.

While the present invention has been exemplified with siRNAs to MYC, Lamin and CXCR4, it is understood that the present complexes may be adapted to other siRNAs. In particular, it is contemplated that siRNAs to oncogenes including, ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES can be delivered to cells according to the present material and methods. The siRNAs can be designed to target the desired RNA by obtaining a target sequence from GenBank and using commercially available software to design the appropriate siRNA.

In the Examples below, carbon nanotubes were solubilized in aqueous phase by amphiphilic molecules, namely phospholipids, particularly PEG-phospholipids. U.S. Pat. No. 6,270,806 to Liversidge, et al., issued Aug. 7, 2001, entitled "Use of peg-derivatized lipids as surface stabilizers for nanoparticulate compositions," discloses methods adaptable for making suitable PEG-phospholipids. That disclosure, hereby incorporated by reference, describes PEG-phospholipid, PEG-cholesterol, PEG-cholesterol derivative, PEG-vitamin A, or PEG-vitamin E surface stabilizer adsorbed on the surface of the drug, whereas in this case the material is adsorbed on the surface of the nanotube.

CXCR4 siRNA has been transferred to three types of T-cells by SWNT and high levels of silencing efficiencies have been obtained. This is surprising in that lipofectamine has no transfection effect to T-cells since human T-cells are widely known to be inert to liposome based transfection agents, as are human primary cells and dendritic cells. This is thought to be because of the difference in cell membrane compositions. The force induced cellular uptake of carbon nanotubes are believed to come from other sources. The fact that longer hydrophilic chains on the surface of tubes make them more inert to cellular uptake leads us to consider that the hydrophobic interaction (not electrostatic interactions) between nanotubes and cell membrane may be the main force inducing the uptake of carbon nanotubes.

SWNT-siRNA conjugates as described below were made through cleavable disulfide linkage. siRNA cargoes can be released inside cell lysosomes by enzymatic cleavage of disulfide bonds. Highly efficient siRNA delivery was achieved by SWNT transporters with a more potent RNAi functionality than a widely used transfection agent, lipofectamine. These previous efforts lead us to consider modified SWNT-siRNA conjugates as another potential choice for T-cells siRNA transfection.

Example 24

Modification and Characterization of SWNT Conjugates

Figure 7A:
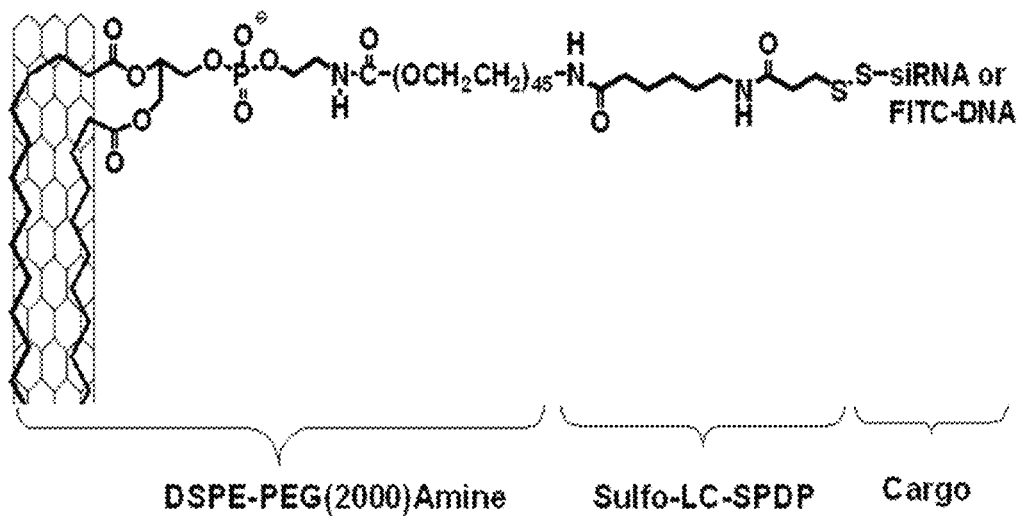
FIG. 7A is a schematic showing a functionalization structure scheme of the SWNT-SS-siRNA/DNA conjugates and 7B is a bar graph showing flow cytometry data of three T cell lines (H9 cells, CEM.NK cells and Sup-T1 cells) incubated with lipofectaime-DNA at 37° C. (first bar), SWNT-SS-DNA at 37° C. (second bar) or SWNT-SS-DNA at 4° C. (third bar). Mean fluorescence intensities of cells (vertical axis) were measured after 6 hours incubation.
Figure 7B:
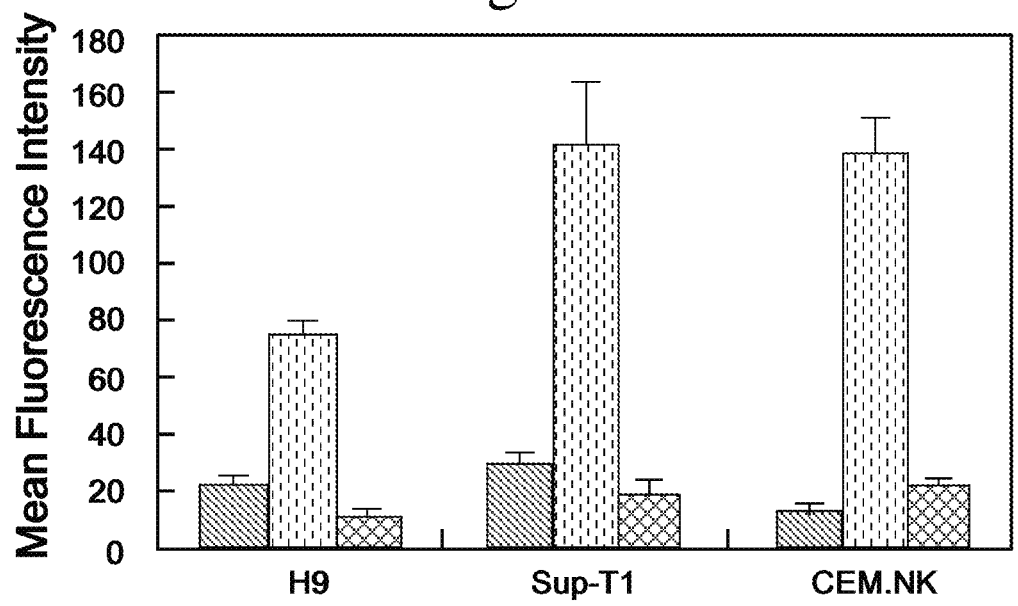

Hipco SWNTs were solubilized in aqueous phase by amine terminated polyethylene glycol (PEG)-grafted phospholipids, giving a highly stable nanotubes solution in the buffer as well as in the cell medium. The two carbon-hydrogen chains of the phospholipids tightly bind around the hydrophobic carbon nanotubes surface, while the hydrophilic PEG chains render nanotubes water-soluble. Thiol modified DNA or siRNA molecules were linked to the terminal amine groups via cleavable disulfide bonds by Sulfo-SPDP linker (FIG. 7a). As demonstrated in the previous examples, disulfide bonds can be cleaved inside cell lysosomes by enzymatic reaction so that the cargoes can be released and undertake their biofunctionalities. Atomic force microscope images showed short individual tubes with an average length around 150 nm. The complex comprises DSPE-PEG (distearoylphosphatidyl-N-(3-carboxypropionylpolyoxyethylene succinyl)ethanolamine-polyethylene glycol 2000) with sulfo-LC-SPDP (Sulfosuccinimidyl 6-(3'-[2-pyridyldithio]-propionamido) hexanoate cross linker) to the nucleic acid (SiRNA) active moiety. These modified carbon nanotubes are very stable in the cell medium. These SWNTs bioconjugates were used afterward in DNA and siRNA delivery.

Hipco SWNT was suspended by DSPE-PEG(2000) Amine (1,2-Distearoyl-sn-Glycero-3-Phosphoethanolamine-N-[Amino(Polyethylene Glycol)2000]) (Avanti Polar Lipids) and modified by Sulfo-LC-SPDP (Pierce) as described in connection with FIG. 4. Excess phospholipid or SPDP linker was removed by centrifuge filters with 100 kD molecular weight cut off (Millipore). The nanotube conjugates were then re-suspended in PB S for conjugation with thiolated biological molecules including SH-DNA or SH-siRNA.

5'-thiol modified siRNAs with the following sequence was synthesized by Dharmacon Research:

(SEQ ID NO: 3)
CD4, 5'- Thiol-GAUCAAGAGACUCCUCAGUdGdA-3' (sense), (SEQ ID NO: 4)
5' -ACUGAGGAGUCUCUUGAUCdTdG-3' (anti-sense);

(SEQ ID NO: 5)
5'- Thiol-GCGGCAGCAGGUAGCAAAGdTdT-3' (sense), (SEQ ID NO: 6)
CXCR4, 5'-CUUUGCUACCUGCUGCCGCdTdT-3' (anti-sense).

The fluorescently labeled oligonucleotide DNA was synthesized by Stanford PAN Biotechnology Facility: 5'-Thiol-C6-CATTCCGAGTGTCCA-FITC-3'. (SEQ ID NO: 2)

All the thiolated siRNAs and DNA used in this work were treated with dithiothreitol (DTT) for 2 hours and then desalted by Sephadex G25 MicroSpin column (Amersham) immediately before usage. It is preferred to pre-treat thiol-siRNA or DNA first with DTT to make sure that any -s-s- species in the sample is converted to siRNA-SH or DNA-SH needed for conjugation to nanotubes via disulfide linkage.

The conjugation reaction was allowed to last overnight and the resulting solution was then ready for further experiments.

Example 25

Labeled DNA Oligonucleotide Delivery by SWNTs to Human T Cell Lines

MAGI-CCR5 is a HeLa-CD4 line that expresses CCR5 and has an integrated copy of the HIV-1 long terminal repeat-driven β-d-galactosidase reporter gene, further described in Chackerian B, Long E M, Luciw P A, Overbaugh J. J. Virol. 1997; 71:3932-3939. Magi-CCR5 cells were grown in DMEM supplemented with 10% fetal bovine serum (FBS) and 100 U/ml penicillin, 100 µg/ml streptomycin, 0.25 µg/ml fungizone, 300 µg/ml L-glutamine, 0.2 mg/ml G418; 0.1 mg/ml hygromycin B; and 1 µg/ml puromycin. Three T cell lines, H9 cells, CEM.NK cells and Sup-T1 cells were grown in RPMI-1640 supplemented with 10% fetal bovine serum, 300 µg/ml L-glutamine and 50 µg/ml gentamicin. All cell lines were kindly provided by NIH AIDS Research & Reference Reagent Program.

As a study of labeled DNA uptake, we first linked fluorescent-labeled DNA oligonucleotides (FITC-DNA instead of siRNA) to SWNT conjugates by disulfide bonds as described in Example 24. From confocal microscope imaging, it was shown after incubation with SWNT-SS-DNA conjugates at 37° C. for 6 hours or 24 hours, cells showed obvious fluorescence. We noticed that after incubation for 6 hours, cells had membrane fluorescence signals as well as bright dots inside. While after 1-day incubation, most fluorescence was located inside cells. We also used commercial oligonucleotide transfection agent lipofectamine 2000 as a comparison to transfect the same amount of DNA. Very weak fluorescence presented on or inside cells after 24 hours incubation. We did the same incubation using SWNT-SS-DNA conjugates at 4° C. and observed no obvious fluorescence (confocal data not shown). This phenomenon suggests an endocytosis mechanism, as described above, for T-cell uptake as well. For confocal microscopy, cells were washed with PBS twice and then imaged directly on the chambered cover-glass or glass slide using a Zeiss LSM 510 confocal microscope.

As a quantitative investigation, flow cytometry experiment was performed to measure the mean fluorescence of cells after those treatments. Beside H9 cells, two other human T-cell lines, CEM.NK and Sup-TI, were used and showed the same trend as we observed from confocal images. In contrast to lipofectamine, which showed no noticeable oligonucleotide DNA delivery effect to T-cell lines, carbon nanotubes had the ability to transport DNA into T-cells, very likely through endocytosis mechanism. We obtained flow cytometry data of three T cell lines incubated with (a) lipofectaime- DNA at 37° C., (b) SWNT-SS-DNA at 37° C. or (c) 4° C. Mean fluorescence intensities of cells were measured after 6 hours incubation. The fluorescence intensities of each cell under condition (b) were 3-4 times higher than either condition (a) or (c), which were about equal.

Example 26

CXCR4 siRNA Delivery

After we succeeded in DNA oligonucleotide delivery, a real bio-functional siRNA delivery was tried for human T-cells. Although down regulation of primary cell surface maker CD4 can inhibit HIV-I infection, CD4 receptor is not a practical target for HIV gene therapy due to its essential role in immunological function. Chemokine co-receptors CXCR4 and CCR5 are also required for viral entry during infection with T-cell tropic X4 or macrophage tropic R5 HIV-1 viral strains, respectively. Because no essential physiological function has been found for these two co-receptors, they are promising targets for HIV therapies. We thus chose CXCR4 as the target. Three human T-cell lines were used again. Cells were incubated with SWNT-SS-siRNA as well as lipofectamine-siRNA mixture.

H9, CEM or Sup cells were plated in 48 well plates with 100,000 cells per well. The SWNT conjugates was added to the cell medium with a final SWNT concentration at 2-3 mg/l, DNA or siRNA concentration at 500 nM. The cells were incubated at 37° C. in a 5% CO2 environment for certain periods of time and washed with PBS before analysis. Lipofectamine 2000 (Invitrogen) was used to compare the transfection efficiency according to manufacture's instructions. Briefly lipofectamine was incubated with DNA or siRNA at room temperature for 30 min in Opti-MEM buffer. The lipofectamine-siRNA mixture was then added to the cell medium under the same conditions as above, with [lipofectamine]=1 mg/L and [DNA]/[siRNA]=500 nM in the incubation.

After three days incubation, cells were stained by PE labeled anti-CD4 antibody and assayed by flow cytometry. For RNAi samples, phycoerythrin (PE)-conjugated CXCR4 monoclonal antibody was used for staining. Data were acquired and analyzed on FACScalibur with CellQuest software (Becton Dickinson, Franklin Lakes, N.J.). Dead cells were stained with propidium iodide and excluded from the data analysis. Significant down regulation of CXCR4 expression (over 80%) was observed for cells incubated with SWNT-SS-siRNA conjugates, while lipofectamine-siRNA gave no observable silencing effect. These results are consistent with the T-cells DNA delivery results, in which carbon nanotubes showed obvious oligonucleotide DNA delivery effect but lipofectamine did not. We then investigated the time dependence of siRNA delivery by SWNTs. We incubated cells with SWNT-siRNA conjugates for different periods of time and performed the assay on the third day. Incubation time is an important factor in terms of silencing efficiency. The silencing efficiency increased with the elongation of incubation time.

As shown in FIG. 8, relative CXCR4 expression level of control cells (first bar), lipo-siRNA treated cells after 3 days incubation (second bar), NT-SS-siRNA treated cells after 1 day (third bar), 2 days (fourth bar) or 3 days (fifth bar) incubation showed significantly lower CXCR4 expression under NT-SS-siRNA treatment of one or more days.

Example 27

C-myc siRNA Delivery

The ability of SWNT to penetrate inside T-cells for transport and delivery of siRNA cargos was explored for the siRNA-mediated silencing of an oncogene. Oncogenes are genes that are responsible for causing abnormalities leading to the development of cancer cells. One of the most severe aspects of cancer is the rapid cell growth and acute, deregulated proliferation of affected cells. Methods to treat cancer cells have been largely focused on identifying and targeting growth receptor factors to achieve some level of control on the growth cycle of the cells. Another strategy that is gaining popularity is to induce disruption in the transcription factor of oncogenes. The MYC family of oncogenes has been found to be common to a wide variety of human cancers and is highly deregulated into such cells. In particular, in cancer cells, the myc gene is always turned on such that aggressive cell division and proliferation take place as well as the cells gaining immunity towards regular cell death pathways. Myc knockdown by RNA interference is a potential solution that can be explored for regulating the cell proliferation and cell fate of cancer cells.

To this end, SWNT-SS-siRNA$_{myc}$ conjugates were prepared with for siRNA targeted to myc knockdown as described earlier. The c-myc siRNA duplex was synthesized by Qiagen with a protected thiol group at the 5' end of the sense strand. The sense sequence used was (SEQ ID NO: 7)
5'-GAA CAU CAU CAU CCA GGA CdTdT-3'.

The SWNT-SS-siRNA conjugates were prepared as described earlier.

These conjugates were used to treat T-cell lymphoma cells, 4188 cells, which were derived from mice overexpressing human myc. Control experiments were also performed where the 4188 cells were exposed to a mixture of SWNT and siRNA$_{myc}$ (no covalent linkage), to lipofectamine-siRNA$_{myc}$ complex or to the antibiotic doxicycline (DOX). The 4188 cells used in this experiment had been previously engineered to be tet-regulatable such that the myc gene can be turned off by treatment with DOX.

The 4188 cells are non-adherent cells, typically cultured in RPMI 1640 medium supplemented with fetal bovine serum, penicillin/streptomycin and betamercaptoethanol. The cells were engineered to have tet-regulatable MYC, which can be regulated by the antibiotic doxicycline (DOX). 4188 cells are further described at Jain, M. et al. Sustained loss of a neoplastic phenotype by brief inactivation of MYC. *Science* 297, 102-104 (2002).

Typical incubations were carried out by incubating 4188 cells with the NT conjugates for periods ranging from 12-14 h at 37° C. and 5% $CO_2$ atmosphere. In addition to our positive incubation with our disulfide containing conjugate, SWNT-SS-siRNA$_{myc}$ (typical [NT] ≈20 nM and [siRNA] ≈500 nM in incubation), control incubations were also carried out with DOX at a concentration 2 ng/mL, commercially available transfecting agent lipofectamine-myc complex and finally with a mixture of SWNT suspension and myc siRNA solution.

Figure 9A:
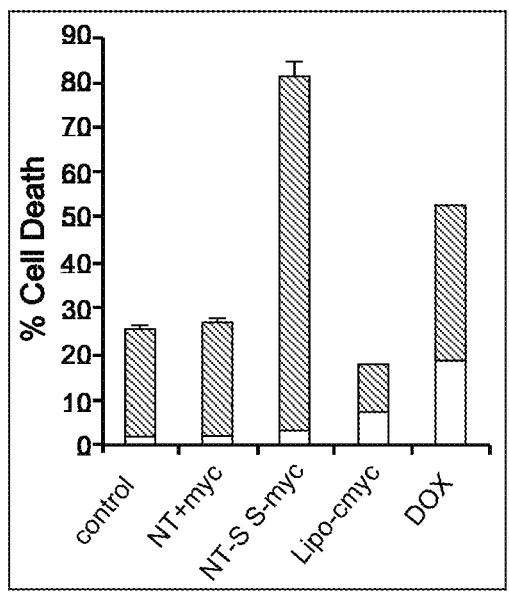
FIG. 9A-9B is a pair of graphs showing viability of cells treated with cmyc—nanotube conjugates. (9A) and the corresponding cell population (9B); the level of cell death was monitored by cell cytometry as the cells were stained by Annexin-V-FITC and propidium iodide (PI). Cells positive for only Annexin-V-FITC account for cell death via apoptosis (clear) whereas cells positive for either PI only or both PI and Annexin-V account for necrotic cells (hatched). The highest level of cell death was observed for NT-SS-myc conjugates.

Upon treatment with SWNT-SS-siRNA$_{myc}$ for approximately 24 h, a net decrease in the cell population was observed. As shown by light microscopy images in FIG. 4*b*, the cell density of SWNT-SS-siRNA$_{myc}$ treated cells is dramatically lower than that of untreated control cells. In order to further investigate this disruption of cell density, the cell proliferation and viability of the 4188 cells were investigated following incubation with SWNT-SS-siRNA$_{myc}$ conjugates (FIG. 9*a*). Consistent with the low cell density observed for the 4188 cells treated with the SWNT conjugates, the highest level of cell death was observed in these cells. Both Annexin-V FITC and propidium iodide were used as markers for cell death. Annexin-V is commonly used for the detection of cell death via apoptosis, whereas propidium iodide is a generic marker for other cell death pathways. The cells treated with the non-covalent mixture of SWNT and siRNA$_{myc}$ (i.e., simple mixture of SWNT-PL-PEG-NH$_2$ with siRNA$_{myc}$) displayed a cell death level that was comparable to that of control untreated cells.

The cell proliferation was determined by using the CellTiterA96 assay (Promega). The assay is MTS-based and relies on colorimetric detection of formazan by UV-VIS spectroscopy at 490 nm. Formazan is the product of successful reduction of the MTS compound by living cells and the amount of formazan present in the cell suspension is directly proportional to the number of living cells. For this study, the MTS assay was used to determine a standard curve for the cell population of 4188 cells. This curve was then used to determine the number of cells for the various incubation conditions.

Cell death was monitored in the cells by cell cytometry. Annexin-V FITC was used to stain cells that died via the process of apoptosis, while propidium iodide was used to detect other generic cell death pathways.

Figure 9B:
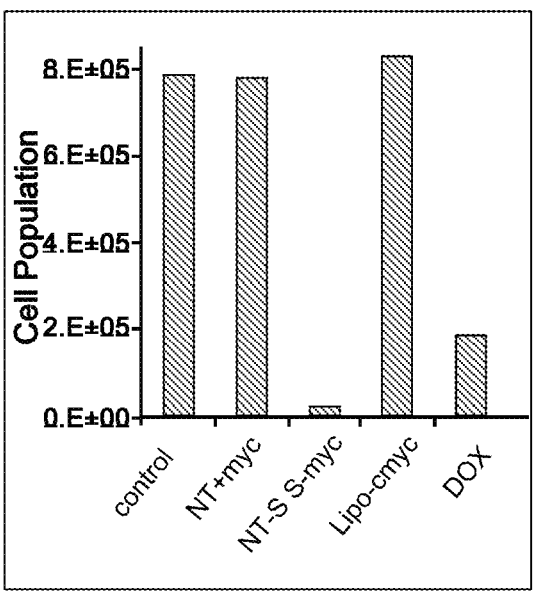

As expected the DOX treatment induced some reduction in the cell density, but at a level that was inferior to that of the SWNT-SS-siRNA$_{myc}$ treatment. The proliferation of the cells was also examined by the use of a colorimetric MTS-based assay. The cell populations were thus determined for the various conditions and consistently indicated that there was a dramatic decrease in the cell density for cells exposed to the SWNT conjugate, at a level that was superior to that of DO X treated cells (FIG. 9b). In order to verify that the decrease in cell viability and proliferation was in fact a result of the knockdown of myc in the lymphoma cells, western blots were performed on the respective cellysates. The myc band was absent for the SWNT-SS-siRNA$_{myc}$ and DOX treated cell. The presence of myc was assessed at two different time points, and from the western blot was seen that the SWNT conjugate was more effective in turning off the myc gene at the 24 h time point than the DOX.

As expected the DOX treatment induced some reduction in the cell density, but at a level that was inferior to that of the SWNT-SS-siRNA$_{myc}$ treatment. The proliferation of the cells was also examined by the use of a colorimetric MTS-based assay. The cell populations were thus determined for the various conditions and consistently indicated that there was a dramatic decrease in the cell density for cells exposed to the SWNT conjugate, at a level that was superior to that of DO X treated cells (FIG. 9b). In order to verify that the decrease in cell viability and proliferation was in fact a result of the knockdown of myc in the lymphoma cells, western blots were performed on the respective cellysates. The myc band was absent for the SWNT-SS-siRNA$_{myc}$ and DOX treated cell. The presence of myc was assessed at two different time points, and from the western blot was seen that the SWNT conjugate was more effective in turning off the myc gene at the 24 h time point than the DOX.

Example 28

Cellular Raman Mapping of Carbon Nanotubes

The cellular internalization of carbon nanotubes was also measured with Raman spectroscopy. Single walled carbon nanotubes have a strong G band Raman peak around 1600 cm$^{-1}$, which gives us a clue to the direct tracking of nanotubes. Cellular Raman intensity maps can be obtained based on the SWNT G band intensities at different positions on the cell after carbon nanotubes internalization. SWNT was suspended at the same concentration with two types of phospholipids with different hydrophilic PEG chain lengths, 2000 Dalton and 5000 Dalton. After overnight incubation, we observed much weaker Raman signal on H9 cells incubated with the latter SWNT conjugates (longer PEG) compared with the those incubated with the former one (shorter PEG). We also made SWNT suspension with both positively charged amine-terminated phospholipids and negatively charged carboxyl terminated phospholipids. After H9 cellular uptake, no obvious difference of average Raman intensities was observed on cells. Combining these results, we believe that the functionalization of carbon nanotubes can influence their cellular uptake significantly. Longer hydrophilic chains on nanotubes surface make nanotubes more inert and allow much lower uptake. Charges of SWNT conjugates are not important for T-cell lines. Considering the inertness of highly positive lipofectamine agent to T-cells, this is understandable and may due to the special properties of the T-cell membrane.

Cells were incubated with SWNT overnight, washed and re-suspended in PBS. A drop of cells suspension was put between two plastic coverslides and observed under Raman microscope. After focusing the laser on the cell, Raman mapping was performed and the data were processed by matlab software. Raman intensity maps were obtained based on the G band intensities at different positions on the cell. In order to get a quantitative result, the average G band intensity was calculated for each cell and about 20 cells were mapped for each sample to get a statistic distribution.

Example 29

Delivery to Human Primary Cells

Peripheral blood mononuclear cells (PBMCs) were derived from a patient and kindly provided by Dr. Mark Winters. The cells were isolated by Ficoll-Hypaque gradients from donor's blood and cultured in RPMI-1640 containing 10% FBS and 10 U Interleukin-2 (R&D system). A Peripheral Blood Mononuclear Cell (PBMC) is a blood cell having a round nucleus, such as a lymphocyte or a monocyte. These blood cells are a critical component in the human immune system to fight infection and adapt to intruders. HIV viruses infect CD4+ T lymphocytes, which are included in PBMCs. PBMCs are known to be extremely hard-to-transfect by liposome based transfection agents. We first investigated the DNA delivery ability of carbon nanotubes. PBMCs were incubated with either SWNT-DNA-FITC conjugates or lipofectamine-DNA-FITC mixture for 24 hours and washed twice with PBS before confocal microscope imaging. The presence of fluorescent labeled DNA inside most of PBMCs indicated high level of SWNT-DNA uptake as shown by fluorescence microscopy (data not shone). In contrast, lipofectamine has no obvious DNA delivery effect.

In terms of siRNA delivery, the same SWNT-siRNA$_{CXCR4}$ conjugate was used to treat the PBMCs. After 3 days incubation, up to 60% of CXCR4 silencing efficiency was obtained as shown by flow cytometry (data not shown), which was surprising, considering the large differential in types of PBMCs. No silencing effect was observed by using lipofectamine 2000 transfection agent.

Example 30

Delivery of Polynucleotides to Cells, Exploiting Enzymatic Cleavage in Cells

As described, the present functionalization approach involves first making stable aqueous suspensions of short SWNTs by non-covalent adsorption of phospholipid molecules with polyethyleneglycol (PL-PEG, MW of PEG=2000) chains and terminal amine or maleimide groups (PL-PEG-NH2 or PL-PEG-maleimide, FIG. 7a). Both DNA and RNA cargos contain a thiol functional group and a 6 carbon long spacer at the 5' end of the DNA or RNA. The PL-PEG binds strongly to SWNTs via van der Waals and hydrophobic interactions between two PL alkyl chains and the SWNT sidewall, with the PEG chain extending into the aqueous phase to impart solubility in water. The amine or maleimide terminal on the PL-PEG immobilized on SWNT can then be used to conjugate with a wide range of biological molecules. For incorporation of a disulfide bond, we employed a heterobifunctional cross-linker Sulfosuccinimidyl 643'-[2-pyridyldithio]-propionamido) hexanoate (sulfo-LC-SPDP) for any thiol-containing biomolecule that was linked to the terminal sulfide or disulfide to afford SWNT-PL-PEG-SS-X, where "X" is the cargos. Specifically, in this example, we formed DNA (15-mer DNA with fluorescence label Cy3) and -SiRNA. For control experiments, we also prepared SWNT-PL-PEG-X conjugates with no disulfide linkage by conjugating X to SWNT-PL-PEG-maleimide.

Hipco SWNTs were sonicated extensively (1-1.5 h) in a solution of 1,2-Distearoyl-sn-Glycero-3-Phosphoethanolamine-N-[Amino(Polyethylene Glycol)2000] (Avanti Polar Lipids). The phospholipid molecule contained a polyethylene glycol chain (45 units) terminated with either an amine group (PL-PEG-NH2) or a maleimide group (PL-PEG-maleimide). The typical PL-PEG concentration used was in the range of 0.1-1 mg/mL. The suspension was then filtered through a membrane filter (Whatman, pore size 100 nm) to remove excess phospholipids, rinsed thoroughly with H2O and re-suspended in either H2O or buffer. The suspension was centrifuged at 24,000 g for 6 h to remove impurities and large nanotubes bundles that aggregated as the sediment. The supernatant was collected and re-centrifuged under similar conditions, and the sediment was again discarded. The nanotubes present in the supernatant (after the two rounds of centrifugation) were short with tube lengths mainly in the range of 50-300 nm as revealed by AFM imaging (See FIG. 1). Both AFM imaging and UV-vis-NIR spectroscopic characterization revealed high purity of SWNTs in the final solution of SWNTs.

Preparation of disulfide-X (SWNT-PL-PEG-SS-X). 2.5 mg of sulfosuccinimidyl 6-(3'-[2-pyridyldithio]-propionamido)hexanoate (sulfo-LC-SPDP, Pierce) was added to a solution of SWNTs functionalized with PL-PEG-NH2 in 50 mM phosphate buffer (supplemented with 0.15M NaCl, pH=7.4). The mixture was allowed to react at room temperature for 1 h, after which the conjugate was centrifuged through a centrifugal filter with molecular weight cutoff of 100 kD (Millipore) for 5 min twice to remove excess sulfo-LC-SPDP cross-linkers. The nanotube conjugates were then re-suspended in H2O for conjugation with thiolated biological molecules including SH-DNA or SH-siRNA. The DNA sequence used in the current work was fluorescently labeled Cy3-SH-(CH2)6-CATTCCGAGTGTCCA (SEQ ID NO: 2), and the siRNA was targeted to lamin, double stranded with sense sequence 5'-SH-(CH2)6CUGGACUUCCAGAA-GAACAdTdT-3' (SEQ ID NO: 8) and antisense sequence 5'-dTdT-GACCUGAAGGUCUUCUUGU-3' (SEQ ID NO: 9) (no fluorescent labeling of the siRNA). The conjugation was allowed to last overnight and the resulting 1-DNA or 1-SiRNA solution was then ready for further experiments.

Preparation of sulfide linked (maleimide)-X (SWNT-PL-PEG-X). SWNTs dispersed in PL-PEG-maleimide in a phosphate buffer of pH ~8 were mixed with either SH-DNA or SH-siRNA and allowed to react for ~3-4 h at room temperature. The resulting maleimide-DNA or maleimide-SiRNA conjugates (containing no disulfide bonds) were used to compare with the disulfide-counterpart with disulfide linkage.

Upon endocytotic entry, disulfide-containing disulfide-X conjugate can be cleaved by thiol-reducing enzymes aided by the acidic pH in the lysosomes. The released molecules from SWNTs could then be freed from lysosomal lipid vesicles to reach the cell cytosol. Indeed, for HeLa cells incubated in a solution of disulfide-DNA for 24 h in the presence of a blue nuclear dye (Draq 5), confocal microscopy imaging revealed colocalization of fluorescence of Cy3-DNA (red) in the cell nucleus, giving rise to pink fluorescence spots within the nucleus (data not shown). This result suggested the intended disulfide cleaving/releasing of molecular cargos into the cytosol and subsequent nuclear translocation of DNA. It is known that short oligonucleotide delivered to the cell cytosol can readily internalize into cell nucleus. In contrast, for maleimide-DNA conjugates, we observed cellular internalization but no nuclear translocation. This suggested that without releasing of DNA from SWNT transporters, the maleimide-DNA SWNT conjugates accumulated in the peri-nuclear region and were unable to penetrate through the nuclear membrane. Having established in-vitro disulfide cleavage and releasing of molecules from SWNTs, we extended our work to transporting and delivery of SiRNA via SWNTs. We employed a SiRNA known to silence the gene encoding lamin A/C protein present inside the nuclear lamina of cells. Similar to the DNA case, we prepared both disulfide-siRNA and maleimide-siRNA as a phospholipid-PEG-cargo complex. HeLa cells were incubated with disulfide-siRNA ([SWNT] ~10 nM or 1.5-2 mg/L and [siRNA].=50-500 nM, [cell]=40,000/well) for up to 24 h (in the presence of 5% fetal bovine serum), fixed 48-72 h later and stained with anti-lamin and a fluorescently labeled secondary antibody. For comparison, we also employed a commercial transfecting agent lipofectamine for siRNA delivery ([lipofectamine] ~1 mg/L). Confocal imaging revealed significant reduction in lamin A/C protein expression by disulfide-siRNA relative to untreated control cells. silencing of the expression of lamin protein by RNAi. Silencing efficiency of Lipofectamin-siRNA was less than 2-siRNA and 1-siRNA (least for 50 nM and 500 nM SiRNA concentrations (data not shown). Our 1-siRNA exhibits a two-fold advantage over transfection by lipofecamine (for the same 500 nM SiRNA concentration). The cells were fixed and stained with anti-lamin and a fluorescently labeled secondary antibody prior to analysis.

Further, flow cytometry data showed that for a given siRNA concentration, the potency of RNAi or percentage of silencing followed dislufide-siRNA>maleimide-siRNA>Lipofectamine-siRNA. We attribute the higher silencing efficiency of disulfide-siRNA than maleimide-siRNA to active releasing of siRNA from SWNTs by enzymatic disulfide cleavage, which maximize the endosome/lysosome escape of siRNA. Also, the functionality of SiRNA may be less perturbed when in a free released form than when attached to SWNT sidewalls. Our disulfide-siRNA exhibits a two-fold advantage over transfection by lipofecamine (for the same 500 nM SiRNA concentration), a widely employed transfection agent. We attribute this to high surface area of SWNTs for efficient SiRNA cargo loading, high intracellular transporting ability of SWNTs and high degree of endosome/lysosome escape owing to the disulfide approach.

We have also obtained excellent siRNA delivery and silencing result for the luciferase gene with SWNT transporters similarly comprising a phospholipid-PEG-cargo structure.

Example 31

Figure 10A:
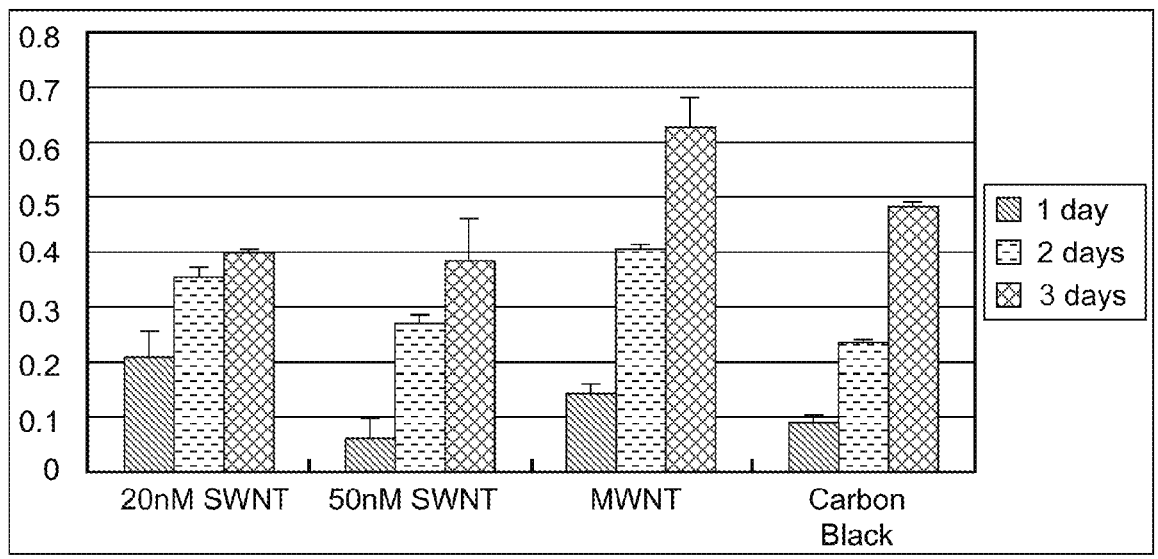
FIG. 10A-10B is a graph showing silencing effect of various nanoparticles with siRNA-PEG-PL delivered to cells (10A) and similar experiments with nanoparticles including polystyrene beads with siRNA to CXCR4.

Cellular Delivery of Different Nanoparticles, Using PL-PEG-s-s-siRNA Conjugates Conjugates as prepared according to Examples 24-27 were made with nanoparticles other than SWNTs. It was shown that MWNTs, carbon black nanoparticles can all be used to make noncovalent PL-PEG-s-s-siRNA conjugates. These are all able to enter cells and deliver siRNA into cells, including T cells and primary cells, cancer cells and stem cells. Referring to FIG. 10A, the silencing effect for these conjugates is shown with reference to SWNT conjugates. The experiments were done with the following:
SWNT: 20 nM and 50 nM.
MWNT: ~20 nM.
Carbon black: 20 nM.

These were all used to make PL-PEG-s-s-siRNA conjugates. The figures shows that MWNTs showed greater RNAi efficiency and kinetics, compared to SWNTs. Carbon black also showed greater silencing efficiency at day 3.

Figure 10B:
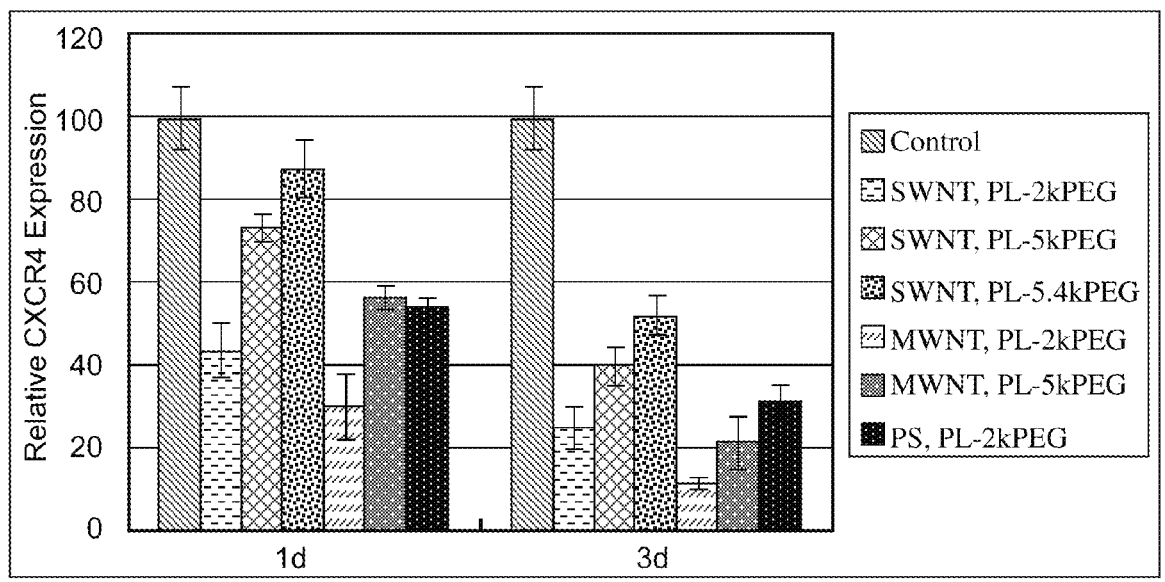

Referring now to FIG. 10B, CXCR4 silencing is shown for different nanoparticles. Polystyrene spheres (PS, 20 nm and 50 nm) were also used to make noncovalent PL-PEG-s-s-siRNA conjugates. They are also able to enter cells and deliver siRNA into cells, including T cells and primary cells, cancer cells and stem cells. The data in FIG. 10B below compares the RNAi effects of PS delivery vs. nanotube delivery.

Example 32

In Vivo Administration

The present compositions may be administered to living organisms, including prokaryotes, eukaryotes, and, in particular, mammals. In vivo work with the above-described complexes first is directed to tests in model animals, such as mice, where the present suspensions would be injected into the tail vein or intraperioneally and cellular uptake would be measured as is known in the art. The Food and Drug Administration has generally agreed that toxicity studies performed largely in mice could safely replace the more costly and time-consuming large animal studies in dog and monkey models.

Currently, the LD10 (the dose of drug lethal to 10% of animals) in mice is tested in a dog model using an MELD10 or mouse equivalent LD10. In the absence of severe toxicity in dogs, phase I trials in humans may begin at one-tenth the LD10 in mice. If severe toxicity is observed in dogs at the mouse LD10, doses are de-escalated to determine the minimally toxic dose in dogs. Clinical studies may then begin at one-third of this dose derived in dogs. Overall, the new NCI toxicology protocol has performed well in predicting safe initial doses for clinical trials while reducing the reliance on and cost of preclinical large-animal toxicology.

This is the use of preclinical pharmacology to guide dose escalation during the conduct of phase I clinical trials. The rationale for pharmacologically guided dose escalation derives from the simple assumption that similar toxicities will occur at similar drug levels in mice and humans. Since both toxicity and efficacy of anticancer drugs are related to total drug exposure, the area under the pharmacokinetic curve (AUC) has been proposed for this purpose.

In general, the AUC is measured in mice following treatment with a given drug at the LD10 dose. This is compared with the AUC in patients entering the first dose of the phase I study, which, as previously discussed, is usually one-tenth the mouse LD10. If the AUC in humans is significantly lower than that observed at the LD10 in mice, dose escalation can be accelerated. The speed with which dose can be escalated depends upon the therapeutic index of a given agent, but two escalation schemas have been proposed. The first, a geometric-mean approach, uses a dose escalation factor equal to the square root of the ratio of the AUC at the mouse LD10 to the AUC in humans at the entry dose level. The second schema continues to double doses at each escalation until the AUC in humans approaches that seen in mice at the LD10. Drug levels would continue to be monitored in all patients on study to be certain that nonlinear kinetics would not cause unexpected toxicities.

This hypothesis, of course, assumes that drug metabolism and end-organ sensitivity to both parent drug and metabolites are similar in mouse and human. Scientists have reported that these assumptions generally are true. In fact, pharmacologically directed dose escalation has been successfully used to accelerate dose escalation in a number of anticancer drugs in phase I clinical trials, including HMBA, merbarone, piraxantrone, and Iodoxorubicin.

The present complexes may be prepared in suspensions suitable for administration to living animals, including humans. Thus, therapeutic proteins such as human growth hormone, bovine growth hormone (for veterinary use), alpha interferon, bone morphogenic protein and the like may be delivered in vivo and into cells through the present complexes.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

The present examples, methods, procedures, specific compounds and molecules are meant to exemplify and illustrate the invention and should in no way be seen as limiting the scope of the invention, which is defined by the appended claims. Any patents or publications mentioned in this specification are indicative of levels of those skilled in the art to which the patent pertains and are hereby incorporated by reference to the same extent as if each was specifically and individually incorporated by reference and for the purpose of describing and enabling the method or material referred to.

What is claimed is:

1. A method for preparing an active agent for delivery to a living cell, comprising the steps of:

(a) providing a hydrophilic polymer linked to the active agent and also linked to a hydrophobic polymer;

(b) adsorbing the hydrophobic polymer onto a nanoparticle, thereby forming a complex with said nanoparticle, wherein the complex is noncovalently adsorbed onto the nanoparticle by hydrophobic interaction with the hydrophobic polymer, and wherein the nanoparticle is a carbon nanotube; and preparing a stable suspension comprising suspended nanoparticles wherein the suspended nanoparticles are comprised in the complex formed in step (b).

2. The method of claim 1 further comprising the step of sonicating the nanoparticles.

3. The method of claim 1 wherein the active agent is selected from the group consisting of polynucleic acids and polypeptides.

4. The method of claim 3 wherein said polypeptide is selected from the group consisting of enzymes, antibodies, peptides, and transcription factors.

5. The method of claim 3 wherein said polypeptide has a molecular weight between 20 kD and 150 kD.

6. The method of claim 3 wherein said polynucleic acid is selected from the group consisting of mRNA, dsRNA, siRNA, synthetic DNA encoding a polypeptide, synthetic DNA complementary to a regulatory region of the cell, and cDNA encoding a polypeptide.

7. The method of claim 1 wherein the hydrophilic polymer is linked to the agent with a cleavable linkage.

8. The method of claim 7 wherein the cleavable linkage is cleavable by lowering the pH in the cell after the complex is delivered in order to release the active agent.

9. The method of claim 1 wherein the active agent induces apoptosis in the cell.

10. The method of claim 1 wherein the active agent is siRNA.

11. The method of claim 10 wherein the siRNA silences an oncogene.

12. The method of claim 10 wherein the siRNA silences a receptor.

13. The method of claim 1 wherein the hydrophilic polymer is polyethylene glycol.

14. The method of claim 1 wherein the hydrophobic polymer is comprised in a phospholipid.

15. The method of claim 1 wherein the linking agent comprises polyethylene glycol-phospholipid.

16. The method of claim 15 wherein said phospholipid is terminated with an amine group for linkage of the hydrophilic polymer.

17. The method of claim 7 wherein the cleavable linkage is selected from the group consisting of disulfide and hydrazone.

18. The method of claim 1 wherein the carbon nanotube is a single walled carbon nanotube.

* * * * *